United States Patent
Young et al.

(10) Patent No.: US 12,016,734 B2
(45) Date of Patent: Jun. 25, 2024

(54) ADJUSTABLE CLAVICLE HOOK PLATE MEASUREMENT GAUGE

(71) Applicant: Acumed LLC, Hillsboro, OR (US)

(72) Inventors: Stephen Young, Portland, OR (US); Caleb Martin, Beaverton, OR (US); Joshua P. Federspiel, Portland, OR (US); Andrew William Seykora, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 526 days.

(21) Appl. No.: 17/224,775

(22) Filed: Apr. 7, 2021

(65) Prior Publication Data
US 2021/0315659 A1    Oct. 14, 2021

Related U.S. Application Data

(60) Provisional application No. 63/006,991, filed on Apr. 8, 2020.

(51) Int. Cl.
*A61B 90/00* (2016.01)
*A61B 17/80* (2006.01)

(52) U.S. Cl.
CPC .............. *A61B 90/06* (2016.02); *A61B 90/39* (2016.02); *A61B 17/80* (2013.01); *A61B 2090/061* (2016.02); *A61B 2090/062* (2016.02)

(58) Field of Classification Search
CPC ...................................... A61B 90/06–2090/069
See application file for complete search history.

(56) References Cited

U.S. PATENT DOCUMENTS

| | | | | |
|---|---|---|---|---|
| 2004/0102776 | A1* | 5/2004 | Huebner | A61B 17/8052 606/291 |
| 2006/0161158 | A1* | 7/2006 | Orbay | A61B 17/8863 606/915 |

(Continued)

FOREIGN PATENT DOCUMENTS

| | | |
|---|---|---|
| CN | 101411640 A | 4/2009 |
| CN | 101411640 B * | 10/2010 |

(Continued)

OTHER PUBLICATIONS

International Search Report corresponding to related International Patent Application No. PCT/US2021/026203 dated Jul. 21, 2021, 3 pages.

(Continued)

*Primary Examiner* — Zade Coley
(74) *Attorney, Agent, or Firm* — K&L Gates LLP

(57) ABSTRACT

A new and innovative medical sizing instrument and method are provided for determining an appropriate depth and/or length of a clavicle hook plate for a patient. The provided medical sizing instrument may enable a surgeon to determine an appropriate hook depth without having to switch between different components, such as a series of templates. In an example, a surgeon may insert the medical sizing instrument into a patient the same as the surgeon would a clavicle hook plate, adjust the hook depth on the medical sizing instrument until a hook depth is obtained that appropriately maintains the anatomical alignment of the patient's clavicle and acromion, and read an indicated depth on the medical sizing instrument. The surgeon may then remove the medical sizing instrument from the patient and select the appropriate clavicle hook plate to insert into the patient.

12 Claims, 16 Drawing Sheets

(56) References Cited

U.S. PATENT DOCUMENTS

| | | | |
|---|---|---|---|
| 2007/0185493 A1 | 8/2007 | Feibel et al. | |
| 2007/0270850 A1* | 11/2007 | Geissler | A61B 17/80 606/326 |
| 2012/0078311 A1* | 3/2012 | Huebner | A61B 17/8085 606/281 |
| 2013/0041375 A1* | 2/2013 | Fierlbeck | A61B 17/809 606/281 |
| 2013/0090695 A1* | 4/2013 | Bernstein | A61B 90/92 606/281 |
| 2018/0344356 A1* | 12/2018 | Zenker | A61B 17/683 |

FOREIGN PATENT DOCUMENTS

| | | | |
|---|---|---|---|
| CN | 201987653 U | * | 9/2011 |
| CN | 201987653 U | | 9/2011 |
| CN | 204274625 U | * | 4/2015 |

OTHER PUBLICATIONS

International Written Opinion corresponding to related International Patent Application No. PCT/US2021/026203 dated Jul. 21, 2021, 4 pages.

International Preliminary Report corresponding to related International Patent Application No. PCT/US2021/026203 dated Oct. 20, 2022, 6 pages.

* cited by examiner

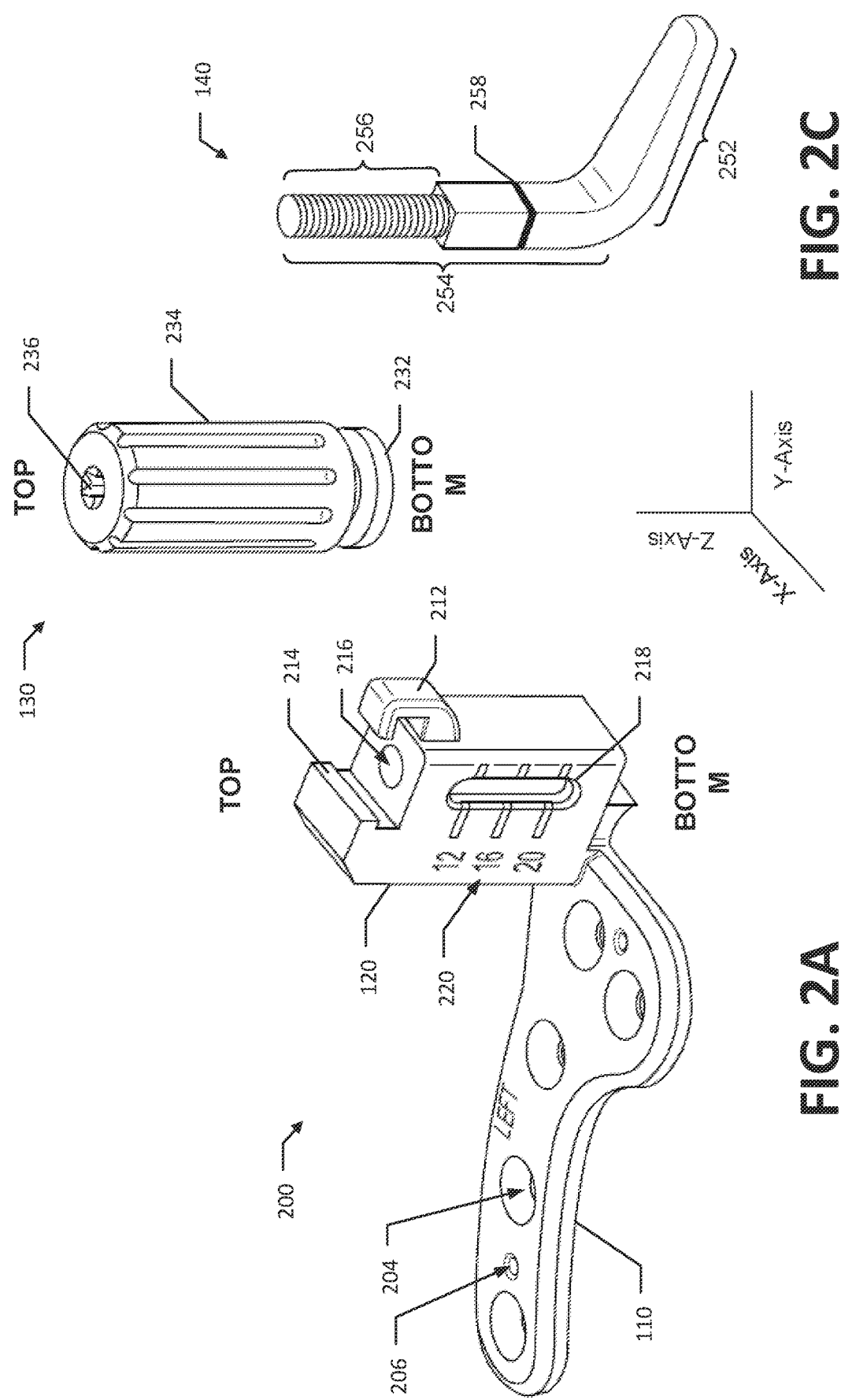

ADJUSTABLE CLAVICLE HOOK PLATE MEASUREMENT GAUGE

PRIORITY CLAIM

The present application claims priority to and the benefit of U.S. Provisional Application 63/006,991, filed Apr. 8, 2020, the entirety of which is herein incorporated by reference.

BACKGROUND

To treat lateral clavicle fractures and acromioclavicular joint disruptions, a clavicle hook plate may be used. A surgeon may make an incision in a patient's shoulder to expose the patient's clavicle and acromioclavicular joint. For lateral clavicle fractures, this may include exposing the outermost part of the clavicle, the fracture site, and the acromioclavicular joint. For acromioclavicular joint disruptions, this may include exposing the acromioclavicular joint and the lateral shaft of the clavicle. The surgeon may then fix the plate portion of the clavicle hook plate to the patient's clavicle while the hook portion contacts the underside of the patient's acromion. The clavicle hook plate, acting as a lever, maintains the anatomical alignment of the patient's clavicle and acromion, and accordingly enables the patient's fracture and/or joint disruption to properly heal. Once sufficient healing has occurred, the surgeon may remove the clavicle hook plate.

When a surgeon treats a patient's lateral clavicle fracture and/or acromioclavicular joint disruption with a clavicle hook plate, the surgeon must use a clavicle hook plate appropriately sized for the patient. For instance, patient shoulder anatomy varies among patients of different heights, ages, genders, or for a variety of genetic reasons. As such, for a clavicle hook plate to properly act as a lever to maintain the anatomical alignment of a given patient's clavicle and acromion, the appropriate length of the clavicle hook plate's plate portion may vary between patients so that the plate portion may be fixed to a sufficient amount of the patient's clavicle. Additionally, the appropriate depth of the clavicle hook plate's hook portion may vary between patients so that the hook portion may contact the underside of the patient's acromion while the plate portion is fixed to the patient's clavicle.

Accordingly, clavicle hook plates are often provided in multiple sizes with different plate portion lengths and hook portion depths. For example, a set of clavicle hook plates may include twelve different sizes, with four different plate portion lengths and three different hook portion depths. Additionally, because clavicle hook plates are contoured in the shape of a patient's clavicle, clavicle hook plates are also provided specifically for a patient's right side and a patient's left side. As a part of the clavicle hook plate implant process, a surgeon must determine the appropriate-sized clavicle hook plate for the respective side of the patient after the surgeon makes an incision in the patient's shoulder to expose the patient's clavicle and acromioclavicular joint.

One way for a surgeon to determine the appropriate-sized clavicle hook plate for a patient is with a series of hook plate templates. The templates are often provided in each available hook depth for the shortest plate length in the set of clavicle hook plates. For example, if a set offers three different hook depths, then the series of templates includes three right-sided templates, one for each hook depth, and three left-sided templates. Thus, the more depth offerings, the more templates there are. The templates often may also be used with a separate component for determining whether the plate length should be longer than the template length.

To determine the appropriate sizing, the surgeon may select and place a first template into the patient and assess whether its size properly maintains the anatomical alignment of the patient's clavicle and acromion. Placing the template into the patient may include provisionally fixing the template to the patient using instruments such as k-wires, plate tacks, and clamps. If the size is not correct, the surgeon may remove the first template, and select and place a second template into the patient to assess whether its size properly maintains the anatomical alignment. The second template may also be provisionally fixed in place.

The process of switching out templates continues until the surgeon selects the template that the surgeon believes best maintains the anatomical alignment of the clavicle and acromion. The more templates there are, the more switching a surgeon may need to do. In some cases, a patient's anatomy may ideally require a hook depth in between the depths offered in the set of clavicle hook plates, and thus may require the surgeon to switch back and forth one or more times between two templates to determine which template best maintains the anatomical alignment. Additionally, each instance the surgeon needs to switch out the templates may include removing the provisional fixtures from one template and then reapplying the provisional fixtures to the new template. Therefore, determining the appropriate clavicle hook plate sizing using a series of templates may be time-consuming and cumbersome for a surgeon.

SUMMARY

The present application provides a new and innovative medical sizing instrument and method for determining clavicle hook plate implant sizing. The medical sizing instrument and method provide a faster, simpler approach for surgeons to determine appropriate sizing for clavicle hook plates in comparison to conventional approaches, such as testing a series of templates. For instance, a surgeon may determine an appropriate hook depth, and in some examples plate length, by inserting the provided medical sizing instrument once and adjusting a hook depth. The surgeon therefore saves time by not needing to switch out and test multiple templates In an example aspect of the present disclosure, a medical sizing instrument for clavicle hook plates includes a tower, a contoured plate, a hook, and a handle. The tower includes an opening extending from a top end of the tower to a bottom end of the tower. The contoured plate extends from the tower and is shaped to match the contour and shape of a clavicle plate implant to be secured to a patient's clavicle bone. The hook includes a first portion at an angle to a second portion with the second portion being positioned through the opening in the tower. The handle may be engaged to adjust a distance between the first portion of the hook and the bottom end of the tower.

In another example aspect of the present disclosure, a method for determining a desired size of the clavicle hook plate includes inserting into a patient, through an incision in a shoulder of the patient, a medical sizing instrument. The medical sizing instrument may be the medical sizing instrument of the first aspect or may be combined with any other aspect. The method then includes adjusting the distance between the first portion of the hook and the bottom end of the tower. A desired distance between the first portion of the hook and the bottom end of the tower is then determined. A clavicle implant may then be selected based on the determined desired distance between the first portion of the hook and the bottom end of the tower.

Additional features and advantages of the disclosed method and apparatus are described in, and will be apparent from, the following Detailed Description and the Figures. The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

BRIEF DESCRIPTION OF THE DRAWINGS

FIG. 2A illustrates an example base portion of the medical sizing instrument of FIG. 1, according to an aspect of the present disclosure.

FIG. 2B illustrates an example handle of the medical sizing instrument of FIG. 1, according to an aspect of the present disclosure.

FIG. 2C illustrates an example hook of the medical sizing instrument of FIG. 1, according to an aspect of the present disclosure.

DETAILED DESCRIPTION

Figure 1:
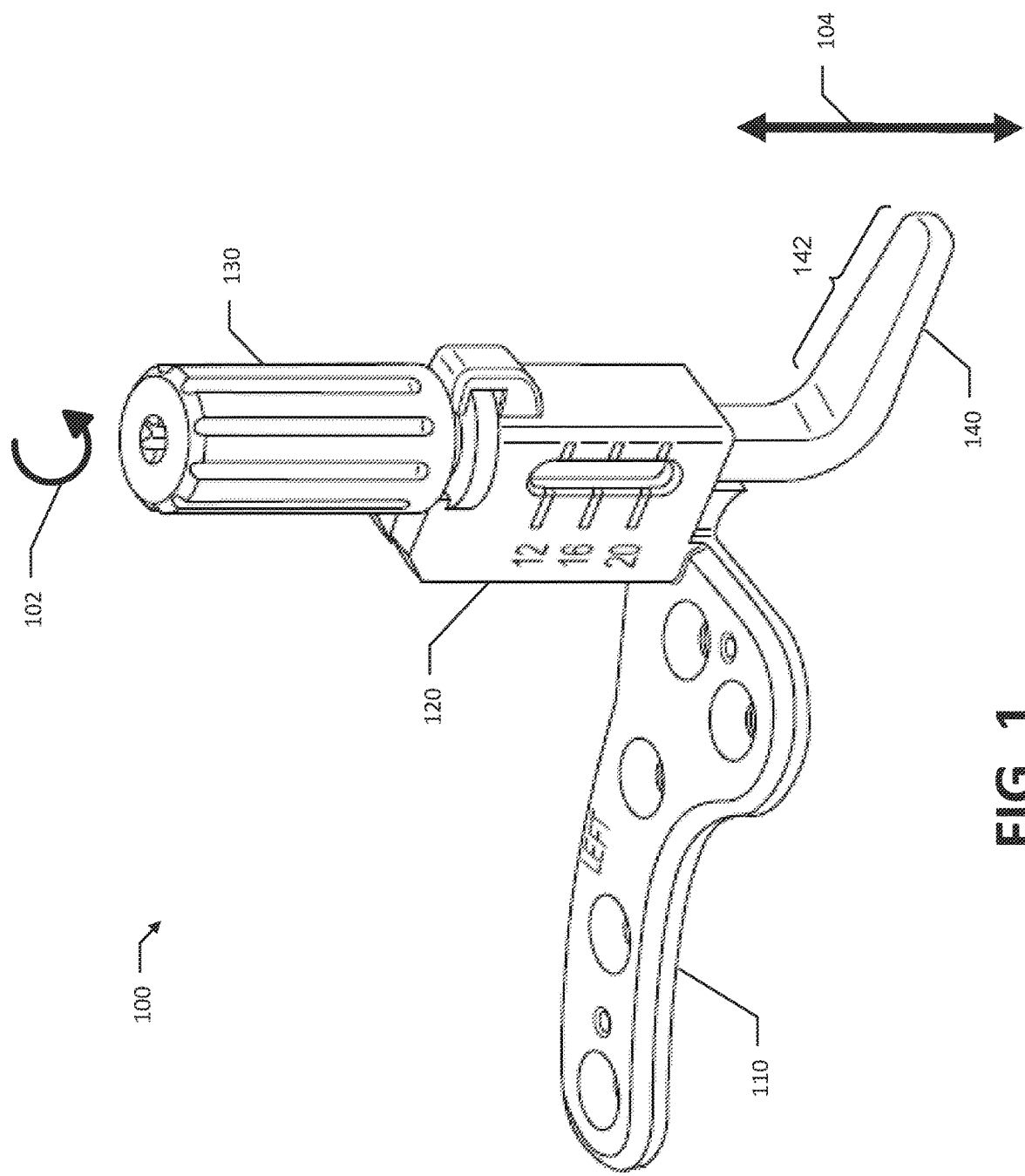
FIG. 1 illustrates a perspective view of an example medical sizing instrument, according to an aspect of the present disclosure.

The present application provides a new and innovative medical sizing instrument and method for determining an appropriate depth of a clavicle hook plate for a patient. In some examples, the provided medical sizing instrument may also include an extendable member for determining the appropriate length of a clavicle hook plate for a patient. The provided medical sizing instrument may enable a surgeon to determine an appropriate hook depth without having to switch between different components, such as a series of templates. For example, the provided medical sizing instrument may include a handle that, when engaged, adjusts the depth of a hook. Therefore, a surgeon may place the medical sizing instrument into a patient the same as the surgeon would a clavicle hook plate, and may adjust the hook depth on the medical sizing instrument until a hook depth is obtained that appropriately maintains the anatomical alignment of the patient's clavicle and acromion. The surgeon may then read an indicated depth on the medical sizing instrument, remove the medical sizing instrument from the patient, and may select the appropriate clavicle hook plate to insert into the patient.

The presently disclosed medical sizing instrument and method thus provide a faster, simpler approach for surgeons to determine appropriate sizing for clavicle hook plates in comparison to conventional approaches, such as testing a series of templates. For instance, a surgeon may determine an appropriate hook depth, and in some examples plate length, by inserting the provided medical sizing instrument once and adjusting a hook depth. The surgeon therefore saves time by not needing to switch out and test multiple templates, which, as described above, may also include removing and reinserting fixture instruments. Given the number of surgical procedures that surgeons perform each day, saved time on each surgery may increase the number of procedures that a surgeon is able to perform in a day. The provided method is also simpler for the surgeon to implement as compared to switching multiple templates, and thus may be more accurate. The provided medical sizing instrument and method may also decrease the amount of items required in an operating room and thus may increase the organization of the operating room and the efficiency of the medical procedure.

In some instances, the presently disclosed medical sizing instrument and method may provide a surgeon with additional information beyond what conventional devices and methods provide. For example, the provided medical sizing instrument allows a surgeon to determine the ideal hook depth that the surgeon believes best maintains the anatomical alignment of the patient's clavicle and acromion. In some cases, the ideal hook depth may be in between the hook depths offered by the clavicle hook plate system the surgeon is using, and thus a clavicle hook plate with the ideal hook depth may not be available. Nonetheless, the additional information regarding what the ideal hook depth is may help the surgeon better determine which available clavicle hook plate the surgeon should use for the patient.

FIG. 1 illustrates a perspective view of an example medical sizing instrument 100, according to an aspect of the present disclosure. The example medical sizing instrument 100 includes a contoured plate 110, a tower 120, a handle 130, and a hook 140. In some aspects, the contoured plate 110 is shaped to match the contour and shape of the implant to be secured to a patient's clavicle bone on the patient's right side. In other aspects, the contoured plate 110 is shaped to match the contour and shape of the implant to be secured to a patient's clavicle bone on the patient's left side. In some examples, the contoured plate 110 may be integrally connected with the tower 120 such that they are one base component. In other examples, the contoured plate 110 may be removable from the tower 120. In such other examples, removing the contoured plate 110 from the tower 120 can enable using the same tower 120 with both a contoured plate 110 contoured for a patient's right side and a contoured plate 110 contoured for a patient's left side. In some examples, the handle 130 may be integrally connected with the tower 120. In other examples, the handle 130 may be removably secured to the tower 120, such as by one or more notches 212, 214 (FIG. 2).

In this example, the hook 140 includes a first portion 142 and a second portion (not illustrated) that are integrally formed with one another at a curved portion. As will be explained in more detail below in connection with FIGS. 2A, 2B, and 2C, the second portion of the hook 140 is placed through an opening in the tower 120 and is removably secured to the handle 130. For instance, the handle 130 may be secured by threaded portions on the exterior of the second portion of the hook 140 and interior of the handle 130. In such an instance, when the handle 130 is rotated, such as in the direction of the arrow 102, the interaction between the threaded portions, and the handle 130 being integrally or removably secured to the tower 120, causes the hook 140 to translate in one of the directions of the double-sided arrow 104. For example, when the handle 130 is rotated in a clockwise direction, this may cause the first portion 142 of the hook 140 to move upward, towards the bottom end of the tower. And when the handle 130 is rotated in a counterclockwise direction, this may cause the first portion 142 of the hook 140 to move downward, away from the bottom end of the tower.

FIGS. 2A, 2B, and 2C illustrate an exploded view of the example medical sizing instrument 100, according to an aspect of the present disclosure. Specifically, FIG. 2A illustrates an example base portion 200 that includes a contoured plate 110 and a tower 120. As described above, in some examples, the contoured plate 110 may be formed integrally with the tower 120, and in other examples, the contoured plate 110 may be removably attached to the tower 120. In the illustrated example, the contoured plate 110 is shaped for a patient's left side. Accordingly, in examples in which the contoured plate 110 is shaped for a patient's right side, the contoured plate 110 and the base portion 200 are a mirror image of that illustrated in FIG. 2A. In other examples, the contoured plate 110 may be configured in shapes other than that illustrated which match the contour and shape of an implant to be secured to a patient's clavicle bone.

In some aspects, the contoured plate 110 may include one or more openings, such as the large opening 204 and the small opening 206. The large openings 204 and small openings 206 may be dispersed in various orientations in various examples to be used for temporarily securing the medical sizing instrument 100 to a patient (e.g., to the patient's clavicle bone) with various surgical tools. Only one of each of the large opening 204 and the small opening 206 are indicated in the figure solely for illustrated clarity, though it should be appreciated that the description of the large opening 204 and the small opening 206 may apply equally to each of those illustrated in FIG. 2A. In some examples, the large openings 204 may be spherically counterbored in shape. In other examples, the large openings 204 may be cylindrically counterbored in shape. The large openings 204 may be used with fixation tools for temporarily securing the medical sizing instrument 100, such as olive wires, a clamp, plate tacks, or screws. The small openings 206 may be used with k-wires for temporarily securing the medical sizing instrument 100.

The example tower 120 may include an opening 216 that extends from the top of the tower 120 to the bottom of the tower 120. As will be explained in more detail below, the opening 216 is sized to allow a portion of the hook 140 to be positioned within and through the opening 216.

In some aspects, the tower 120 may include a window 218. The window 218 may enable a surgeon to visibly see a portion of the hook 140 that is positioned through the opening 216, and in particular, may enable the surgeon to visibly see an indicator 258 (FIG. 2C) that is on the hook 140. In various aspects, the tower 120 may include a plurality of markings 220 adjacent to the window 218. For example, the plurality of markings 220 may correspond to the offered hook depths in the clavicle hook plate system. Accordingly, a surgeon may view the indicator 258 on the hook 140 through the window 218 relative to the markings 220 to determine a depth of the hook 140. In other aspects, the medical sizing instrument 100 may include another suitable arrangement of indicators for the surgeon to take a measurement with the medical sizing instrument 100. For example, the hook 140 may include one or more indicators 258 positioned on the hook 140 such that they are visible to the surgeon when the portion of the hook 140 including an indicator 258 exits the tower 120 through the opening 216.

In some examples of the present disclosure, the tower 120 may removably secure a handle 130 (FIG. 2B) so that rotation of the handle 130 causes the hook 140 to translate rather than causing the handle 130 to translate. In such examples, the tower 120 secures the handle 130 so that when the handle 130 is rotated it remains stationary with respect to a direction parallel to the axis about which the handle 130 rotates. For example, the tower 120 may include one or more blocks 212, 214 that removably secure the handle 130 to the tower 120. The blocks 212 and 214 allow the example handle 130 to rotate and to slide freely along the illustrated x-axis, but prevent the example handle 130, when secured, from translating along the illustrated y and z axes. In this way, the example handle 130 may be secured to the tower 120 when in use and may also be removed from the tower 120. Allowing disassembly of the handle 130 from the tower 120 may enable easier cleaning of the medical sizing instrument 100 in some instances.

In some examples of the present disclosure, the handle 130 may be permanently assembled with the tower 120 such that it cannot be removed. For instance, in such examples, a block that surrounds the entire outer perimeter of the handle 130, or a portion of the perimeter of the handle 130, may be manufactured on the tower 120 with the handle 130 in place so that the handle 130 is permanently held in place. Examples in which the handle 130 is permanently assembled with the tower 120 decreases the number of separate components that need to be assembled to use the example medical sizing instrument 100, and thus may increase organizational efficiency for operating rooms.

FIG. 2B illustrates an example handle 130, according to an aspect of the present disclosure. In some aspects, the example handle 130 may include a gripping portion 234 and a securing portion 232. The securing portion 232 may extend from the gripping portion 234 by a portion thinner than both the gripping portion 234 and the securing portion 232. The thinner portion and the securing portion 232 enable the securing portion 232 to be secured by the blocks 212 and 214 on the tower 120. For instance, the blocks 212 and 214 fit in the space between the gripping portion 234 and the securing portion 232 and prevent the securing portion 232 from translating in the illustrated z-axis.

In this example medical sizing instrument 100, the handle 130 is configured such that it may be removably secured to, and adjustable with respect to, the hook 140. For example, the handle 130 may include an interior threaded portion (not illustrated) that extends at least a portion of the interior of the handle 130 from the bottom (e.g., at the securing portion 232) of the handle 130 toward the top of the handle 130. In some instances, the interior threaded portion may extend completely from the bottom of the handle 130 to the top of the handle 130 such that there is an opening on both the bottom and top. In other instances, the interior threaded portion may begin at the bottom of the handle 130 and terminate within the interior of the handle 130 prior to the top end, such that there is only an opening on the bottom. The interior threaded portion is configured to accept a threaded portion 256 (FIG. 2C) on the hook 140. In some instances, the handle 130 may include a notch 236 that enables the handle 130 to be rotated with the use of a tool. For example, the notch 236 may be a female drive feature of a hexalobe screw system that may be used with a male hexalobe driver, though the notch 236 may be shaped for other suitable driver configurations in other examples.

FIG. 2C illustrates the example hook 140, according to an aspect of the present disclosure. The example hook 140 may be shaped to replicate a hook design in a clavicle hook plate system. For example, the hook 140 may be in an L-shape as illustrated and include a first portion 252 integrally formed with a second portion 254. The first portion 252 may be at an angle (e.g., 85, 90, 95, 100, 105 degrees) to the second portion 254. In some aspects, the second portion 254 may be longer than the first portion 252. In other aspects, the second portion 254 may have a length equal to or shorter than the first portion 252.

The second portion 254 is shaped to be inserted through the opening 216 of the tower 120. In some aspects, the second portion 254 may include a portion (e.g., the threaded portion 256) that removably secures the second portion 254 to the handle 130. In various aspects, the second portion 254 of the hook 140 and the opening 216 in the tower 120 are correspondingly shaped to prevent the hook 140 from rotating when the handle 130 is rotated. For example, the second portion 254 and the opening 216 may each have a trapezoidal cross-section thereby enabling the second portion 254 to only be assembled into the tower 120 in one orientation and preventing the hook 140 from rotating when the handle 130 is rotated.

In various aspects, the hook 140 is symmetric and can therefore be assembled into either a right-side base portion 200 or a left-side base portion 200, as described above. For example, a trapezoidal cross-section of the opening 216 in a right-side tower 120 may be flipped 180 degrees as compared to a trapezoidal cross-section of the opening 216 in a left-side tower 120 to accommodate the hook 140.

When the base portion 200, the hook 140, and the handle 130 are assembled, the hook 140 may be translated relative to the base portion 200. In the example medical sizing instrument 100, the hook 140 may be translated by way of a threaded drive, though other translation mechanisms will be described below. In this example, the second portion 254 of the hook 140 includes a threaded portion 256 that is configured to be inserted into the interior threaded portion of the handle 130. The second portion 254 includes a threaded portion 256 sufficient to cause the hook 140 to translate through the desired depth ranges upon rotation of the handle 130. For instance, too short of a threaded portion 256 may not allow the hook 140 to translate through the entire depth range and would not provide sufficient information to a surgeon, but too long of a threaded portion 256 may be unnecessary and may increase production costs and/or interfere with the indicator 258 that is also on the second portion 254. In some examples, the threaded portion 256 of the hook 140 and the corresponding interior threaded portion of the handle 130 may include a large pitch and additional clearance between the internal and external thread forms to allow for quick and easy adjustment of the hook 140 by rotating the handle 130.

Figure 2D:
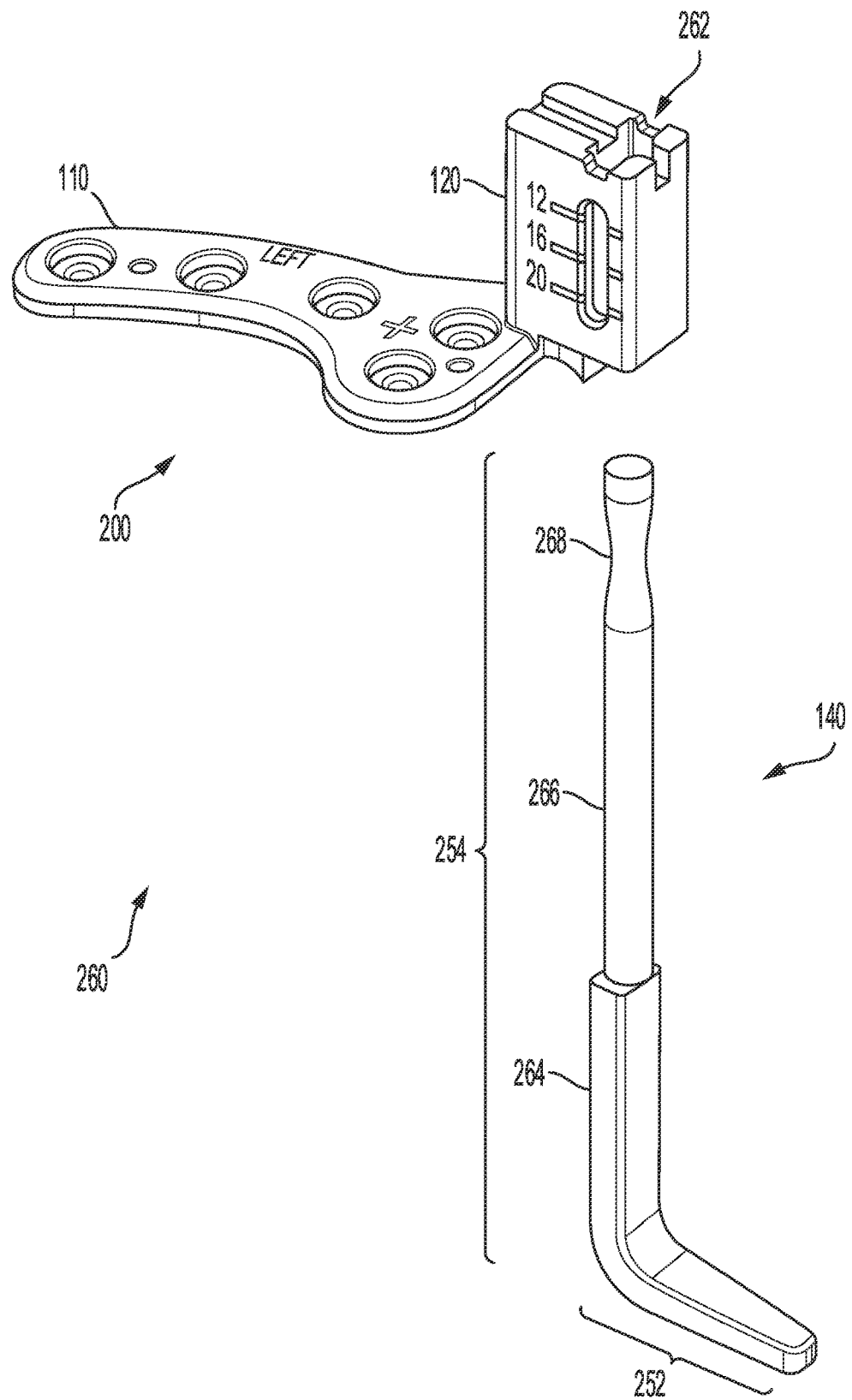
FIGS. 2D and 2E illustrate perspective views of an example medical sizing instrument that includes a sliding hook, according to an aspect of the present disclosure.
Figure 2E:
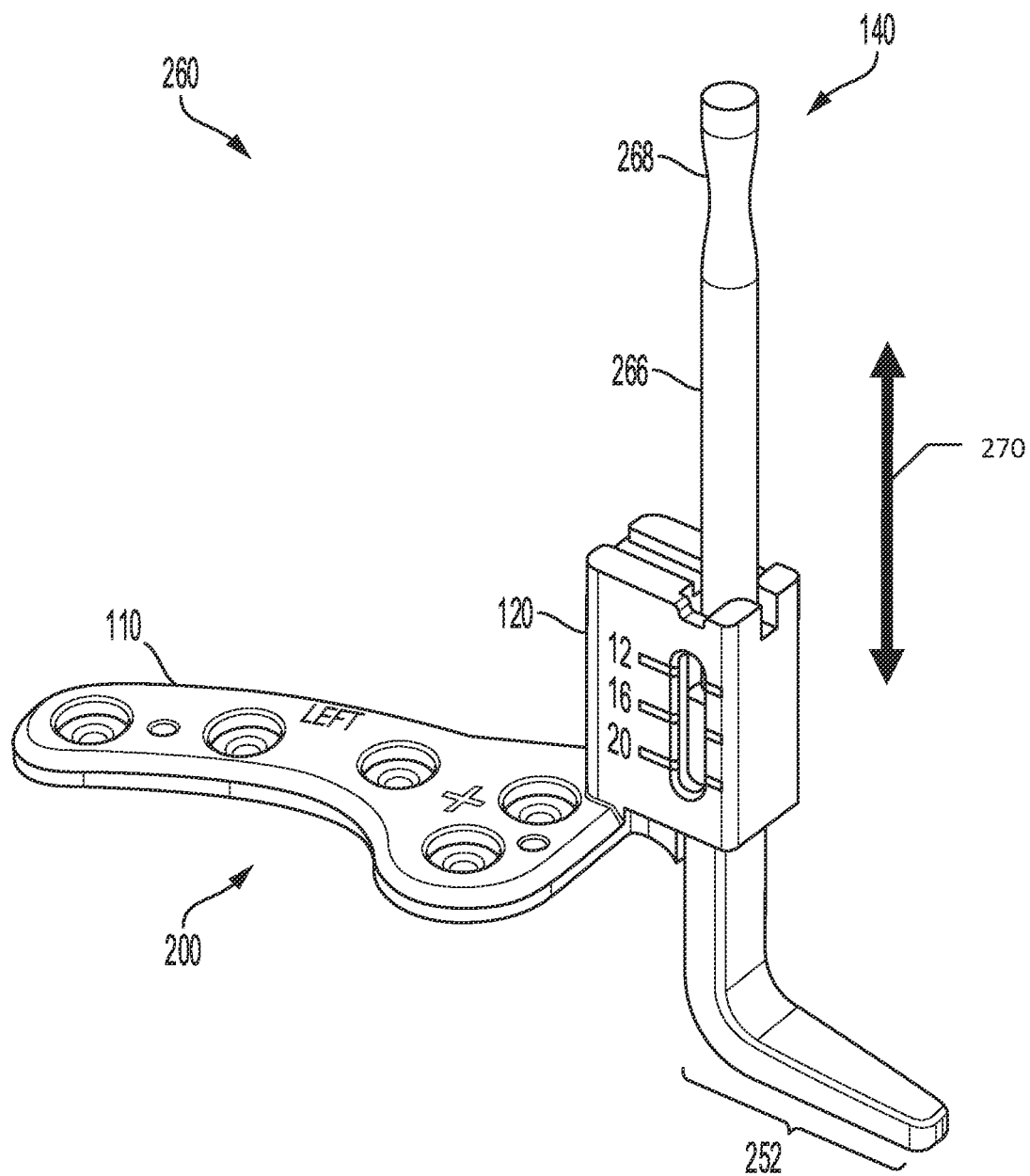

In other aspects, the hook 140 may be translated by way of other mechanisms. For example, FIGS. 2D and 2E illustrate a medical sizing instrument 260 that is configured with a sliding hook mechanism. FIG. 2D illustrates an exploded view of the example medical sizing instrument 260 which includes a base portion 200 and a hook 140. The base portion 200 may include a contoured plate 110 integral with or removably attached to a tower 120. The tower 120 may include an opening 262. The hook 140 includes a first portion 252 and a second portion 254. In this example, the second portion 254 of the hook 140 includes a sliding portion 264, a sliding portion 266, and a handle 268. As shown in FIG. 2E, the hook 140 may be positioned through the opening 262 in the tower 120 and slides as it is pushed and pulled in the directions of the double-sided arrow 270. For example, the opening 262 may be sized such that an interior portion of the tower 120 forming the opening 262 applies force to the sliding portion 264 and/or the sliding portion 266 of the hook 140 when the sliding portion 264 and/or the sliding portion 266 is inserted within the opening 262, thereby generating frictional force. The frictional force may maintain a position of the hook 140 until that frictional force is overcome by pushing or pulling the hook 140 to force the hook 140 to slide. For instance, a medical professional may push and pull the handle 268 to translate the hook 140 and adjust its depth. In other examples, though not illustrated, the hook 140 may be translated relative to the tower 120 by way of a worm gear, a rack and pinion, a cam-and-piston type mechanism, a wheel-and-coupling type mechanism, or other suitable mechanisms. A person having skill in the art will appreciate how these other example translation mechanisms could be implemented in view of the above translation mechanism examples.

Returning to FIG. 2C, in various aspects, the second portion 254 of the hook 140 includes an indicator 258. For example, the indicator 258 may be a laser band around the perimeter of the second portion 254. As described above, when the second portion 254 of the hook 140 is placed through the opening 216 in the tower 120, the indicator 258 may be viewed through the window 218 of the tower 120. When the hook 140 is translated relative to the tower (e.g., the handle 130 is rotated) the indicator 258 on the hook 140 moves within the window 218. Thus, the indicator 258 may be viewed through the window in relation to the markings 220 to determine the depth that the hook 140 is at.

In certain aspects, the provided medical sizing instrument (e.g., the medical sizing instrument 100) may be configured such that the hook 140 may be locked into discrete positions via a locking mechanism. For instance, the discrete positions may be when the indicator 258 of the hook 140 is even with each individual marking of the markings 220 on the tower 120. In such aspects, the locking mechanism is sufficient to maintain the hook 140 in a particular discrete position until a surgeon releases the hook 140. In this way, the locking mechanism may therefore help a surgeon take depth measurements without having the hook 140 incidentally move and alter the measurement reading while the surgeon positions the medical sizing instrument.

Figure 3A:
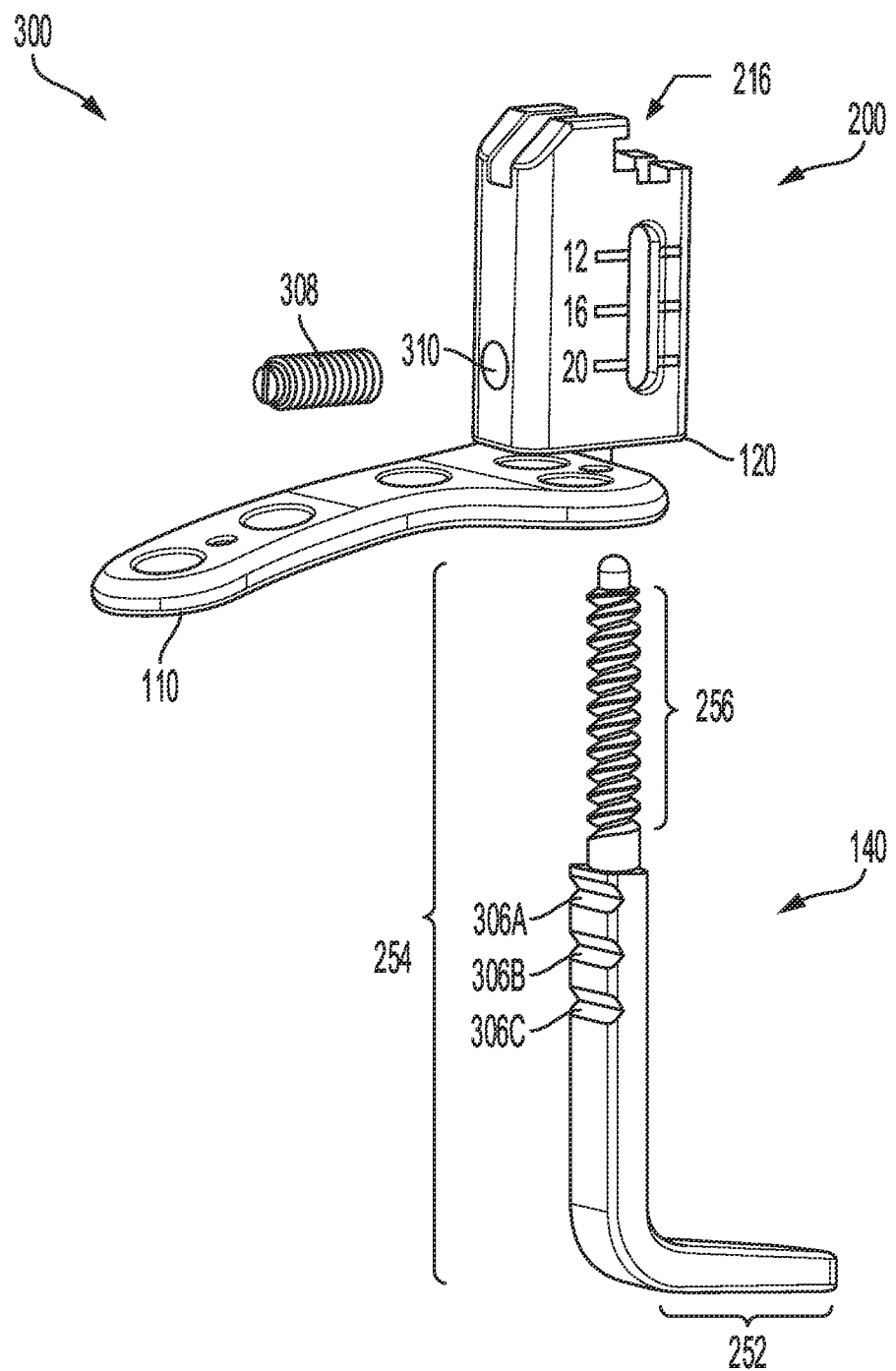
FIG. 3A illustrates a perspective view of an example medical sizing instrument that includes a ball plunger/detent position locking mechanism, according to an aspect of the present disclosure.
Figure 3B:
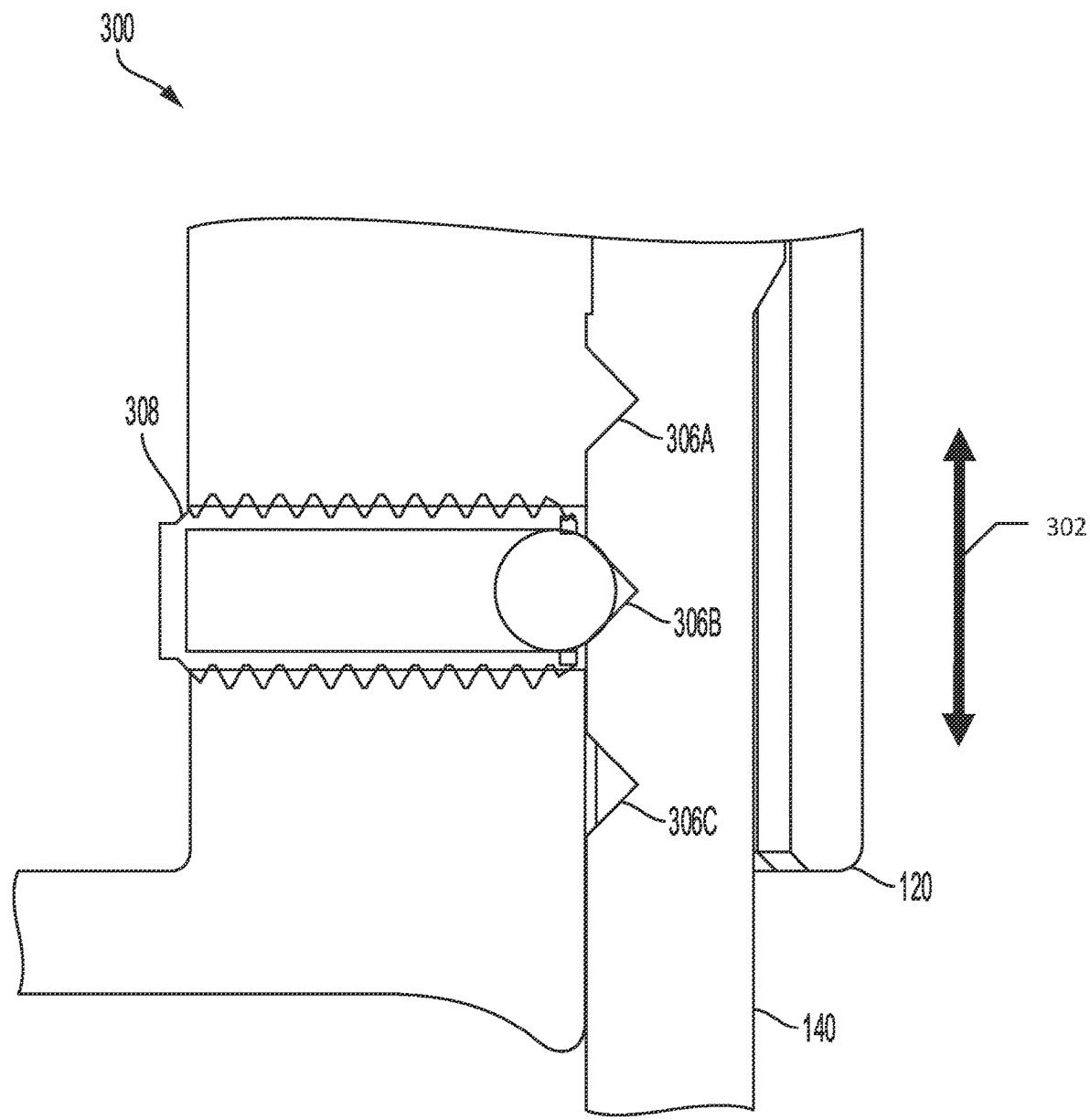
FIG. 3B illustrates a cross section of the example ball plunger/detent position locking mechanism shown in FIG. 3A.

FIG. 3A illustrates an example medical sizing instrument 300 that includes a ball plunger/detent position locking mechanism. The example medical sizing instrument 300 includes a base portion 200 and a hook 140. The base portion 200 may include a contoured plate 110 integral with or removably attached to a tower 120. In some aspects, the second portion 254 of the hook 140 may include a threaded portion 256 for translating the hook 140 via a threaded drive. In such aspects, the medical sizing instrument 300 may include a handle 130 that engages the threaded portion 256. In other aspects, the second portion 254 of the hook 140 may be configured for other suitable mechanisms for translating the hook as described above. In this example, the second portion 254 of the hook 140 may include one or more notches 306A, 306B, and 306C. In at least some aspects, the medical sizing instrument 300 includes a ball detent 308 that is inserted within an opening 310 in the tower 120. When the hook 140 is positioned through the opening 216 of the tower 120, the ball detent 308 may settle into each of the notches 306A, 306B, and 306C as the hook 140 is translated such that the ball detent 308 is positioned at a notch 306A, 306B, or 306C. FIG. 3B illustrates a cross section of a portion of the example medical sizing instrument 300 showing the ball detent 308 settled into and positioned at the notch 306B. A medical professional may translate the hook 140 by applying force to the hook 140, when the hook 140 is assembled in the tower 120, in the directions of the double-sided arrow 302. Applying such force to the hook 140 moves the ball component of the ball detent 308 to enable the hook 140 to translate.

The ball detent 308 settling into a notch 306A, 306B, or 306C provides a medical professional with tactile feedback, for example, in the form of an audible "click" sound and/or in the form of additional resistance to the hook's movement. The ball plunger/detent position locking mechanism may be referred to as a "soft stop" form of feedback because the hook 140 may be translated upon additional force being applied to the hook 140.

Figure 3C:
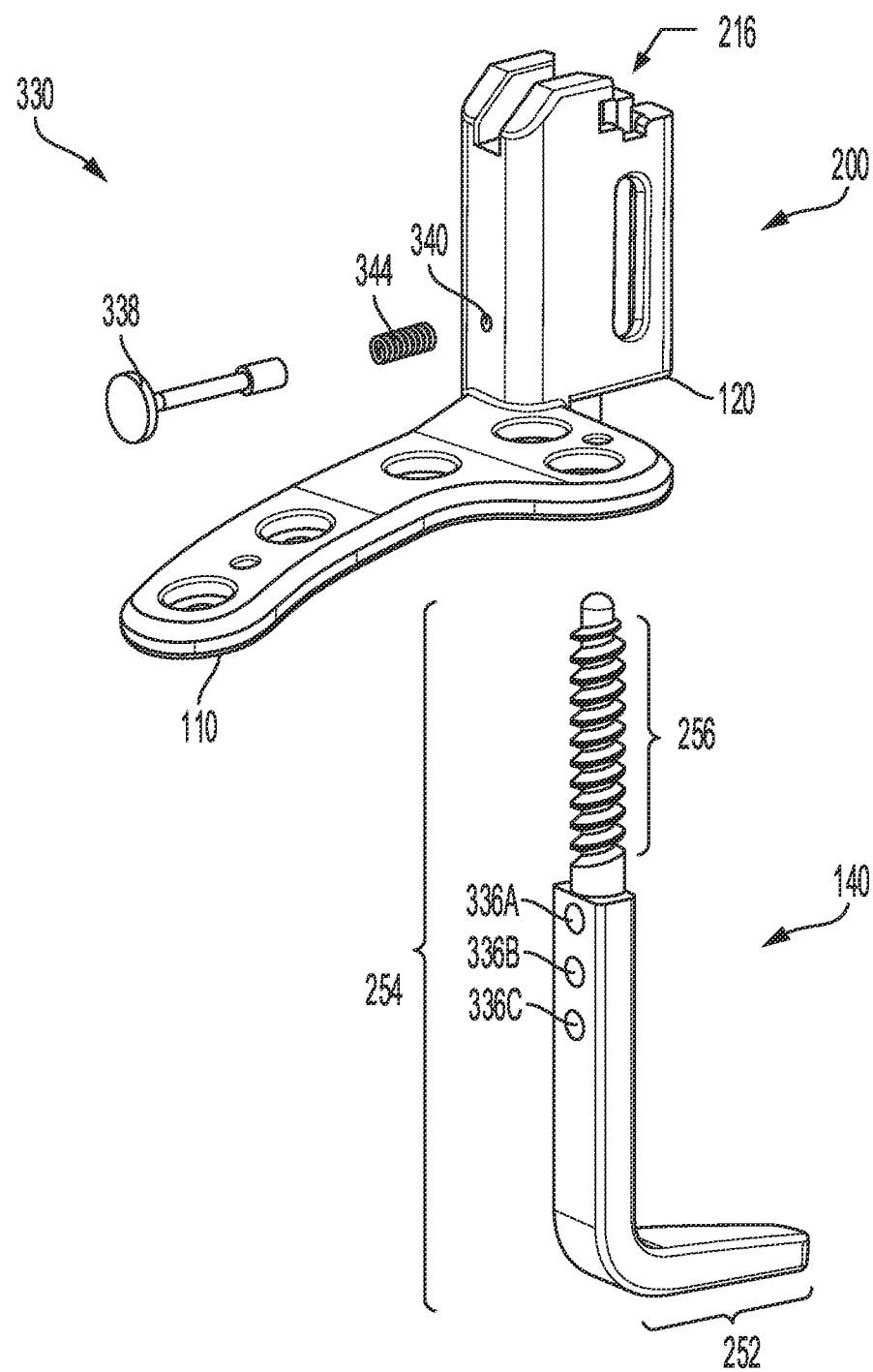
FIG. 3C illustrates a perspective view of an example medical sizing instrument that includes a spring-loaded pin position locking mechanism, according to an aspect of the present disclosure.

FIG. 3C illustrates an example medical sizing instrument 330 that includes a spring-loaded pin position locking mechanism. The medical sizing instrument 330 includes a base portion 200 and a hook 140. The base portion 200 may include a contoured plate 110 integral with or removably attached to a tower 120. In some aspects, the second portion 254 of the hook 140 may include a threaded portion 256 for translating the hook 140 via a threaded drive. In such aspects, the medical sizing instrument 300 may include a handle 130 that engages the threaded portion 256. In other aspects, the second portion 254 of the hook 140 may be configured for other suitable mechanisms for translating the hook as described above. In this example, the second portion 254 of the hook 140 includes one or more notches 336A, 336B, and 336C. In at least some aspects, the medical sizing instrument 330 includes a pin 338 and a spring 344 that are inserted within an opening 340 of the tower 120. When the hook 140 is translated through the opening 216 in the tower 120, the pin 338 moves into a notch 336A, 336B, or 336C due to expansion of the spring 344.

Figure 3D:
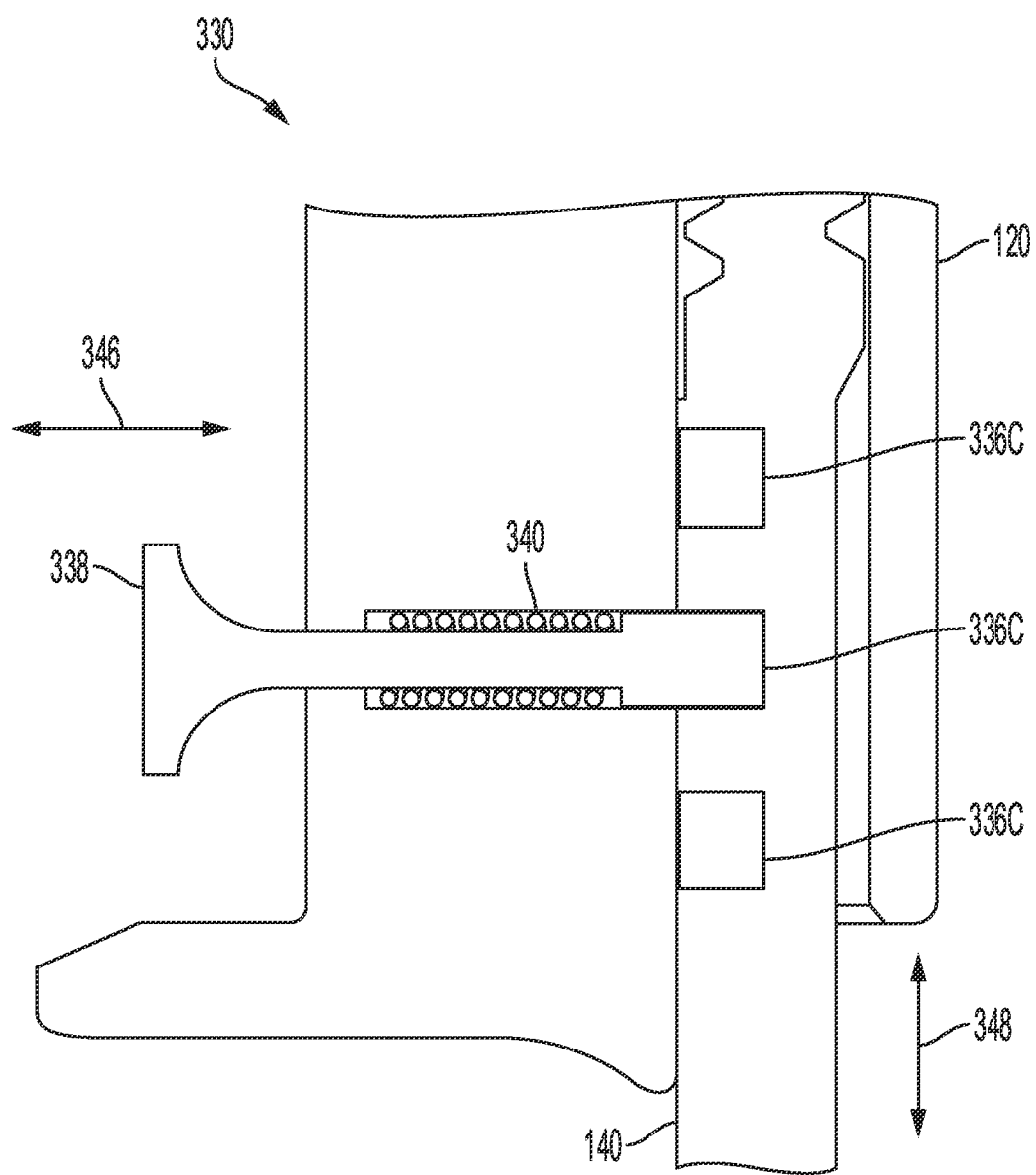
FIG. 3D illustrates a cross section of the example spring-loaded pin position locking mechanism shown in FIG. 3C.

For instance, FIG. 3D illustrates a cross section of a portion of the example medical sizing instrument 330 showing the pin 338 moved into the notch 336B. The pin 338 thereby locks the hook 140 into place, fixing it against movement in the direction of the double-sided arrow 348, until the pin 338 is retracted against the expansion of the spring 344. The pin 338 may be retracted against the expansion of the spring 344, or may move into a notch 336A, 336B, or 336C due to the expansion of the spring 344, in the direction of the double-sided arrow 346. The spring-loaded pin position locking mechanism may be referred to as a "hard stop" form of feedback because a medical professional cannot translate the hook 140 until the pin 338 is retracted. The spring-loaded pin mechanism of the example medical sizing instrument 330 may also be implemented in ways other than the illustrated example, such as by spring-loaded levers, elastic tabs, torsional springs, etc.

Figure 3E:
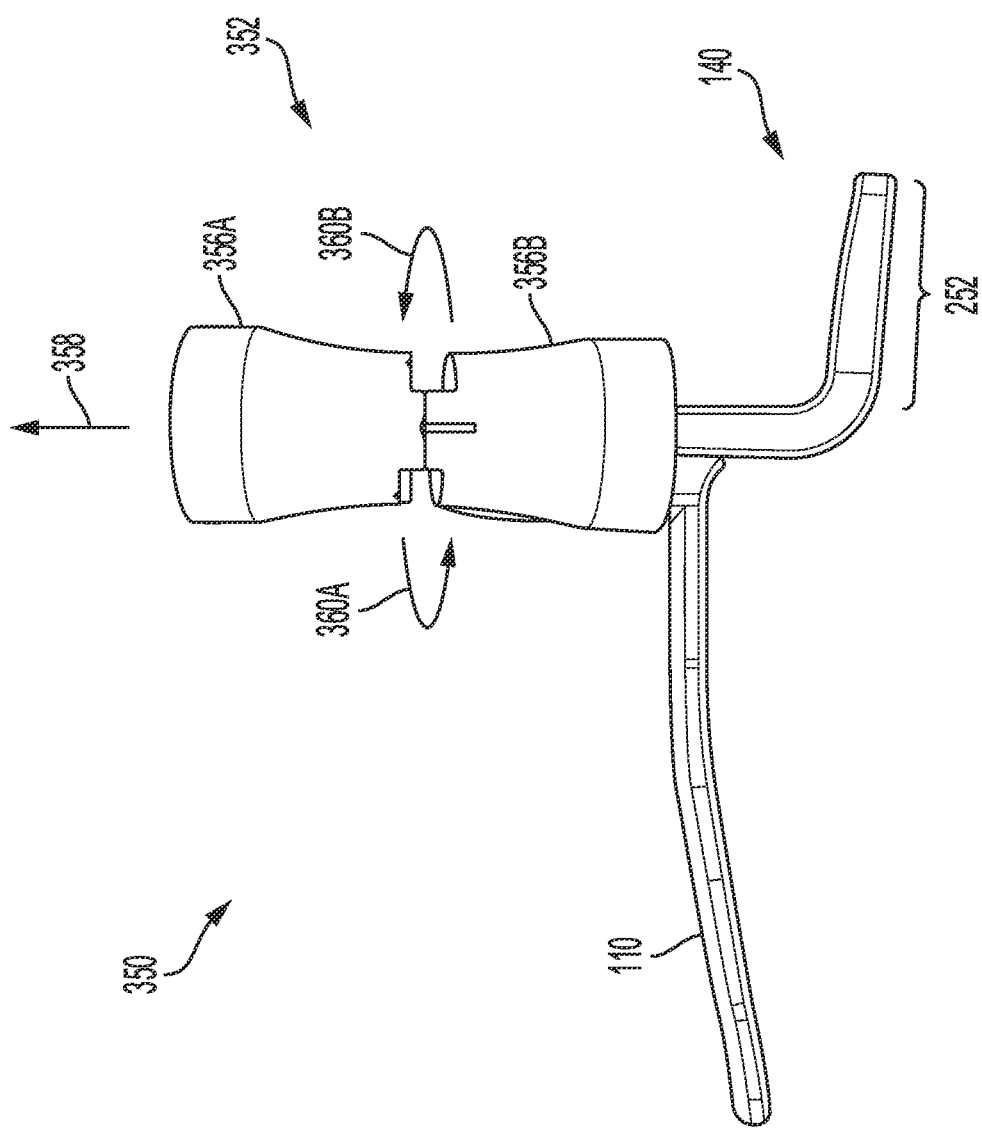
FIG. 3E illustrates a side view of an example medical sizing instrument that includes a spring-loaded stepped tower position locking mechanism, according to an aspect of the present disclosure.

In another example of a position locking mechanism, FIG. 3E illustrates an example medical sizing instrument 350 that includes a spring-loaded stepped tower position locking mechanism. The example medical sizing instrument 350 includes a contoured plate 110, a hook 140, and an example tower 352. The contoured plate 110 may be integral with or removably attached to the tower 352. The tower 352 may include a top component 356A (e.g., a handle) and a bottom component 356B. The top and bottom components 356A and 356B of the tower 352 are spring-loaded and configured such that a distance between the top component 356A and the bottom component 356B may be increased or decreased. A medical professional may pull the top component 356A apart from the bottom component 356B in the direction of the arrow 358 and against the spring contraction. While pulled apart, the medical professional may then rotate the top component 356A relative to the bottom component 356B (e.g., in the direction of the arrows 360A and 360B) and may release the top component 356A to thereby increase or decrease the distance between the top component 356A and the bottom component 356B at discrete increments. As an example, the tower 352 including the top and bottom components 356A and 356B may be configured according to the Biotrak Nail/Pin Plunger (80-0323) of the Biotrak system offered by Acumed®, the Applicant of the present application.

In at least some aspects, the top component 356A may be connected (e.g., removably or fixedly) to the hook 140. As such, the first portion 252 of the hook 140 may translate to discrete positions as the medical professional adjusts the top component 356A relative to the bottom component 356B.

In other examples, though not illustrated, the locking mechanism may be a snap lever/pivot lever, a cam-type mechanism, a smooth post that only has threading close to measurement locations, or any other kind of positive indexing feature on a sliding post with features to register against. A person having skill in the art will appreciate how these other example locking mechanisms could be implemented in view of the above locking mechanism examples.

Figure 4A:
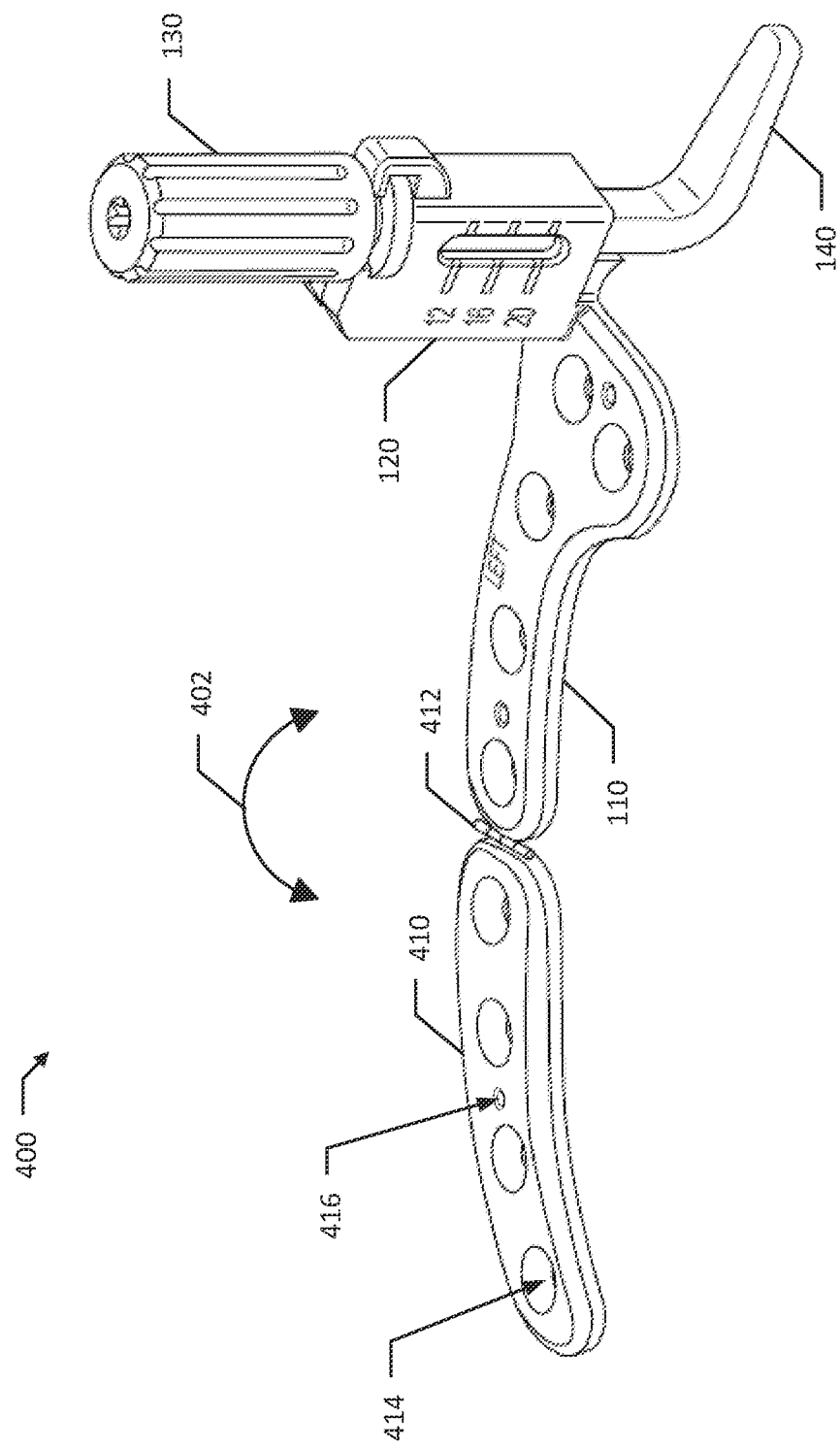
FIG. 4A illustrates a perspective view of an example medical sizing instrument that includes a hinged extendable member for length measurements, according to an aspect of the present disclosure.

In some examples of the present disclosure, the provided medical sizing instrument may be configured to be used for both determining the desired depth of the hook portion and the desired length of the plate portion. FIG. 4A illustrates an example medical sizing instrument 400 for determining both hook depth and plate length, according to an aspect of the present disclosure. The example medical sizing instrument 400 may include a contoured plate 110, a tower 120, a handle 130, and a hook 140 configured according to any of the examples and aspects described above.

The example medical sizing instrument 400 may also include an extendable member 410 that may extend from the contoured plate 110. For example, the extendable member 410 may be rotatably connected to the contoured plate 110 by a hinge 412. In the illustrated example, the extendable member 410 may rotate about the hinge 412 in the directions of the double-side arrow 402. In some aspects, such as the one illustrated, the extendable member 410 may be extended or may be folded flat onto the side (e.g., the side visible in FIG. 4A) of the contoured plate 110 nearest the tower 120. In other aspects, the hinge 412 may enable the extendable member 410 to be folded onto the side (e.g., the side not visible in FIG. 4A) of the contoured plate 110 farthest from the tower 120. Folding the extendable member 410 in this way to a closed position is beneficial for storage to save space. From the closed position, the extendable member 410 may be extended as illustrated for use.

In other examples, the extendable member 410 may have other suitable configurations such that the extendable member 410 may fold into a closed position and extend from the contoured plate 110 in an extended position. For instance, the extendable member 410 may rotate by a hinge in a plane parallel to the contoured plate 110. It will also be appreciated that, while the example medical sizing instrument 400 is shown with a threaded drive mechanism for translating the hook 140 relative to the tower 120, the medical sizing instrument 400 may be configured according to any of the above-described translation mechanisms.

In some aspects, the extendable member 410 may include large openings 414 and small openings 416 for temporarily securing the extendable member 410 to a patient (e.g., to the patient's clavicle bone). The large openings and small openings 416 may be the same as or similar to the large openings 204 and small openings 206 of the contoured plate 110. In some aspects, the extendable member 410 may be contoured in the same manner as the contoured plate 110 such that the extendable member 410, when extended, is a continuation of the contoured plate 110.

Figure 4B:
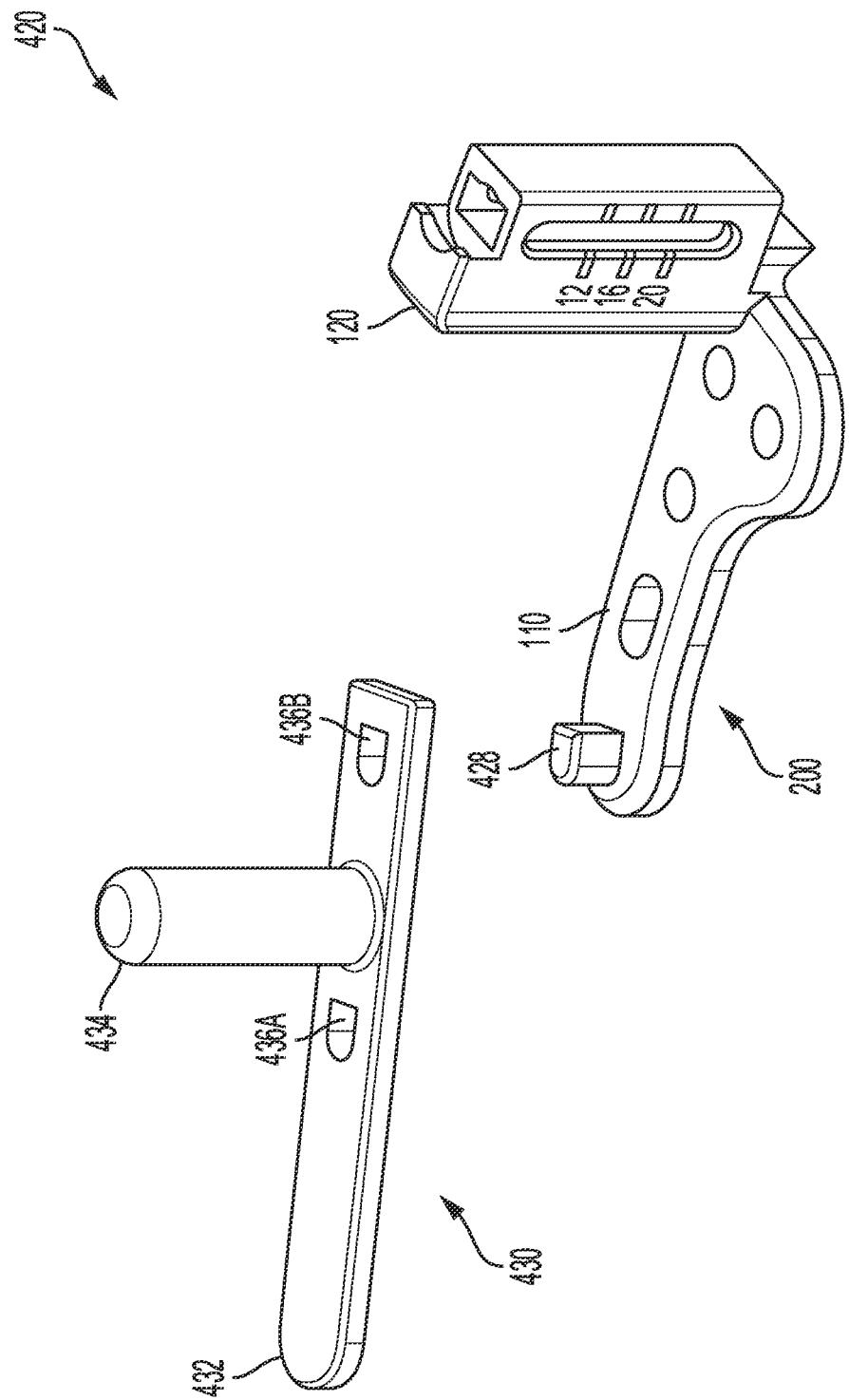
FIG. 4B illustrates an exploded perspective view of an example medical sizing instrument that includes an add-on ruler for length measurements, according to an aspect of the present disclosure.

In another example of an extendable member for determining the desired length of the plate portion, FIG. 4B illustrates a base component 200 and add-on ruler 430 of an example medical sizing instrument 420. The base component 200 may include a tower 120 and a contoured plate 110. Though not illustrated, the medical sizing instrument 420 also includes a hook 140. The tower 120, the contoured plate 110, and the hook 140 may be configured according to any of the examples and aspects described above. In this example, the contoured plate 110 may include a post 428. The removable add-on ruler 430 (e.g., extendable member) of the medical sizing instrument 420 may be coupled with the contoured plate 110 to extend the length of the contoured plate 110.

In various aspects, the add-on ruler 430 may include a base 432. A handle 434 may extend from the base 432. The handle 434 may make it easier for a surgeon to move and manipulate the add-on rule 430. The base 432 in various aspects includes one or more openings 436A, 436B. The add-on ruler 430 may be coupled to the contoured plate 110 by positioning one of the openings 436A, 436B over the post 428. Stated differently, the post 428 is positioned through one of the openings 436A, 436B. In at least some aspects, the post 428 and the one or more openings 436A, 436B may each be correspondingly shaped such that the add-on ruler 430 can only be oriented in a single orientation with respect to an opening 436A, 436B and the post 428. For example, the illustrated half-oval shape of the post 428 and the openings 436A and 436B only allows the post 428 to be inserted through the opening 436A or 436B in a single orientation. The corresponding shape between the post 428 and an opening 436A or 436B also prevents the add-on ruler 430 from rotating when coupled to the contoured plate 110. In this way, the add-on ruler 430 may always be coupled to the contoured plate 110 in a consistent fashion thereby helping a medical professional obtain accurate length measurements.

Figure 4C:
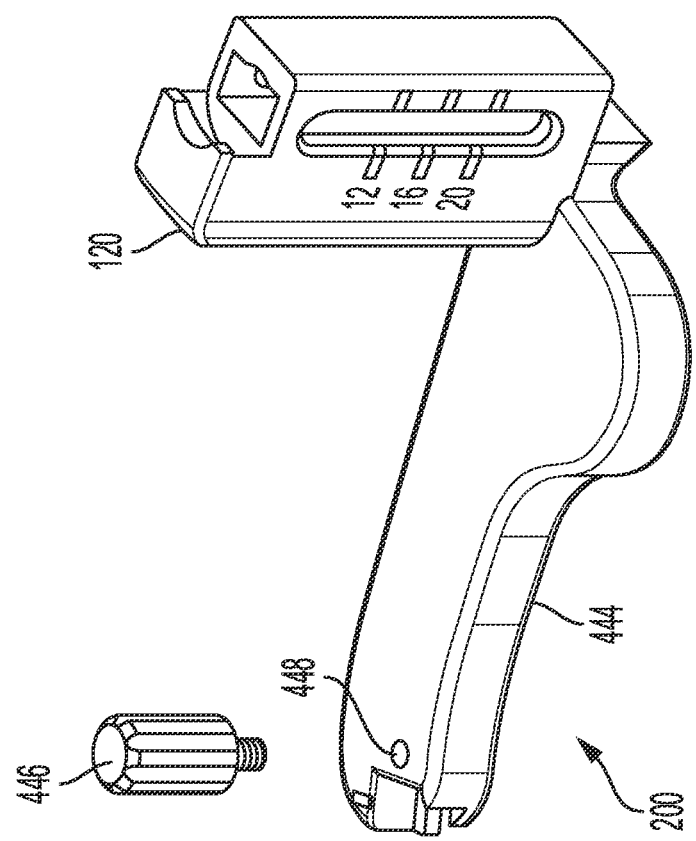
FIGS. 4C and 4D illustrate perspective views of an example medical sizing instrument that includes a sliding member for length measurements, according to an aspect of the present disclosure.
Figure 4C:
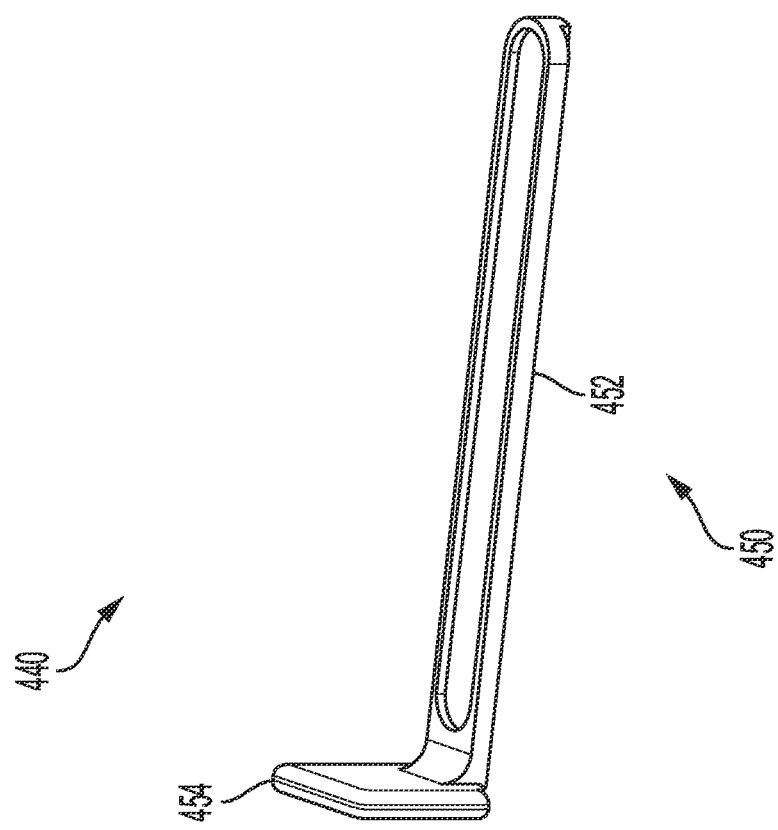
Figure 4D:
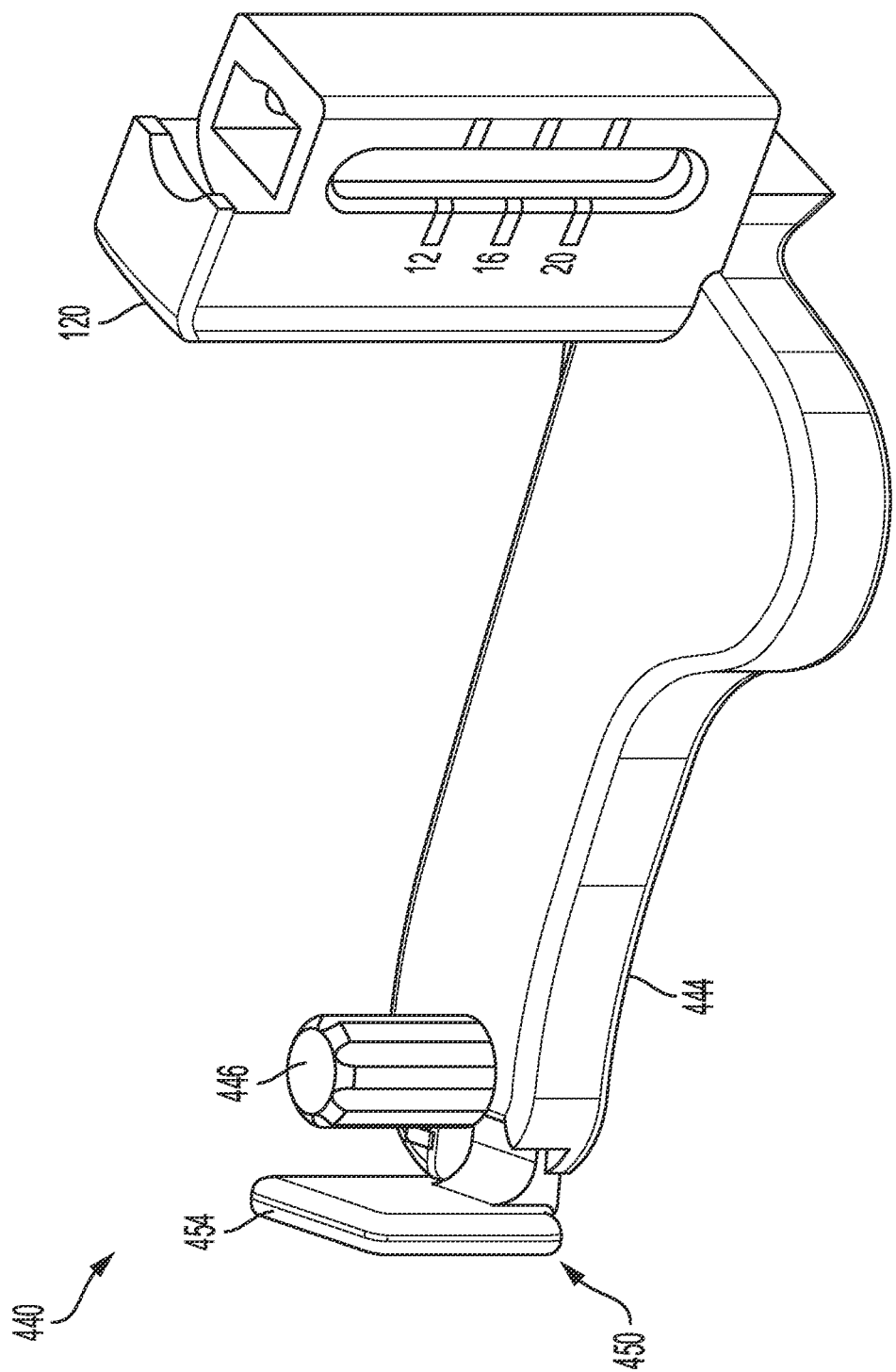

In another example of an extendable member for determining the desired length of the plate portion, FIGS. 4C and 4D illustrate a base component 200, a sliding member 450, and a knob 446 of an example medical sizing instrument 440. The base component 200 may include a tower 120 and a contoured plate 444 in this example. The contoured plate 444 may be integral with or removably attached to the tower 120. In at least some aspects, the sliding member 450 may include a body 452 integral with or attached to a handle 454. Though not illustrated, the medical sizing instrument 440 also includes a hook 140. The tower 120 and the hook 140 may be configured according to any of the examples and aspects described above. The contoured plate 444 may shaped with the contour described above for the contoured plate 110.

FIG. 4C illustrates an exploded view of the medical sizing instrument 440 showing the sliding member 450 apart from the contoured plate 444. The contoured plate 444 includes a chamber (not illustrated) within which the body 452 of the sliding member 450 may be inserted, as shown in the perspective view of FIG. 4D. The knob 446 of the example medical sizing instrument 440 may be adjusted to vary the level of engagement between the knob 446 and the sliding member 450. For example, the contoured plate 444 may include a threaded hole 448 through which a threaded portion of the knob 446 may be positioned. In this example, the greater the knob 446 is tightened, the greater the force the knob 446 places on the sliding member 450 to maintain the sliding member 450 in its position as the result of frictional forces. Conversely, the more the knob 446 is loosened, the less force the knob 446 places on the sliding member 450 and the easier the sliding member 450 slides within the chamber of the contoured plate 444. In other examples, a different suitable mechanism other than the threaded knob 446 may be utilized to maintain a position of the sliding member 450 relative to the contoured plate 444.

In some aspects, such as the one illustrated, the contoured plate 444 does not include any openings (e.g., the openings 204, 206) for fixation tools for temporarily securing the medical sizing instrument 440. In other aspects, the contoured plate 444 may include at least one large opening 204 and/or at least one small opening 206 for fixation tools. In such aspects, the at least one large opening 204 and/or at least one small opening 206 are offset from the chamber of the contoured plate 444 so as to not interfere with the sliding member 450. In at least some aspects, the knob 446 and the sliding member 450 may be removed from the contoured plate 444 entirely (e.g., as illustrated in FIG. 4C), which provides an ease of cleaning.

FIG. 4D illustrates the medical sizing instrument 440 in which the sliding member 450 is positioned almost entirely within the chamber of the contoured plate 444. A medical professional may slide the sliding member 450 out of the chamber a distance sufficient to take measurements. In the illustrated example, the contoured plate 444 is shown without fixation openings as described above in connection with various other embodiments. In other examples, however, the contoured plate 444 may include one or more fixation openings. In some aspects, the sliding member 450 may be configured on top of or below the contoured plate 444 instead of within the contoured plate 444.

Figure 4E:
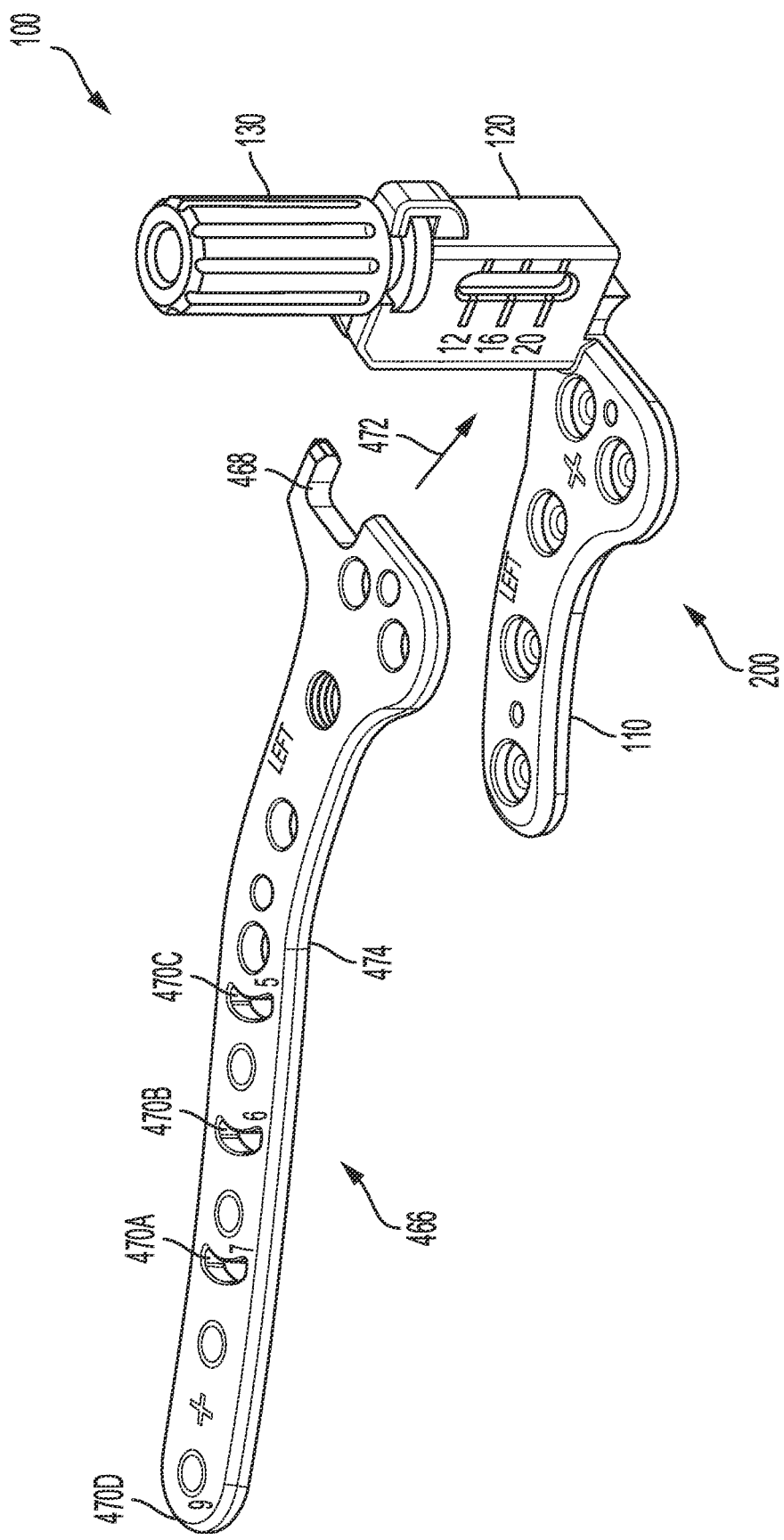
FIG. 4E illustrates an exploded perspective view of an example medical sizing instrument that includes an indexing ruler for length measurements, according to an aspect of the present disclosure.

FIG. 4E illustrates an additional example of a length measuring component that can be used with the provided medical sizing device. In particular, FIG. 4E illustrates an indexing ruler 466 that may be used with the base component 200 of the medical sizing instrument 100. In other examples, the indexing ruler 466 may be used with the base component 200 of the medical sizing instrument 260, 300, 330, or 350. In at least some aspects, a body 474 of the indexing ruler 466 has a length that enables measurements for every plate length in a clavicle hook plate system. For example, the indexing ruler 466 may include the length indications 470A, 470B, 470C, and 470D that each correspond to a different plate length in the clavicle hook plate system. In at least some aspects, the indexing ruler 466 may include a notch 468. A medical professional may position the indexing ruler 466 in the direction of the arrow 472, on top of the contoured plate 110 with a portion of the tower 120 position within the notch 468. The notch 468 is configured to conform to the portion of the tower 120 such that the indexing ruler 466 may be positioned in only a single orientation and is stable when the tower 120 is positioned within the notch 468. The notch 468 therefore allows for accurate positioning of the indexing ruler 466 relative to the hook 140.

Once the indexing ruler 466 is positioned, the medical professional may take length measurements using the indexing ruler 466. In various aspects, the indexing ruler 466 may include fixation openings (e.g., the large openings 204 and the small openings 206) as illustrated. In such aspects, the fixation openings on the indexing ruler 466 may line up with the fixation openings on the contoured plate 110. Accordingly, the indexing ruler 466 and the contoured plate 462 may both be temporarily secured to the patient together in such aspects.

In another example still of an extendable member or length measuring component, the provided medical sizing instrument may include an extendable member that is stored in a rolled configuration and may be rolled out when needed.

Accordingly, a surgeon may position any of the above-described extendable members (e.g., length measuring components) when using the provided medical sizing instrument to determine the appropriate length for the contoured plate. For example, in some instances the appropriate length may be the length of the contoured plate 110 attached to the tower 120, which is typically the shortest length offered in the clavicle hook plate system. However, in other instances, the appropriate length may be longer and thus the extendable member enables the surgeon to determine how much longer so the surgeon can select the appropriate clavicle hook plate for implantation. In some aspects, a surgeon may determine an appropriate contoured plate length without inserting the hook 140 into the tower 120. Stated differently, in an example, the surgeon may determine the appropriate contoured plate length using only the base component 200.

Figure 5:
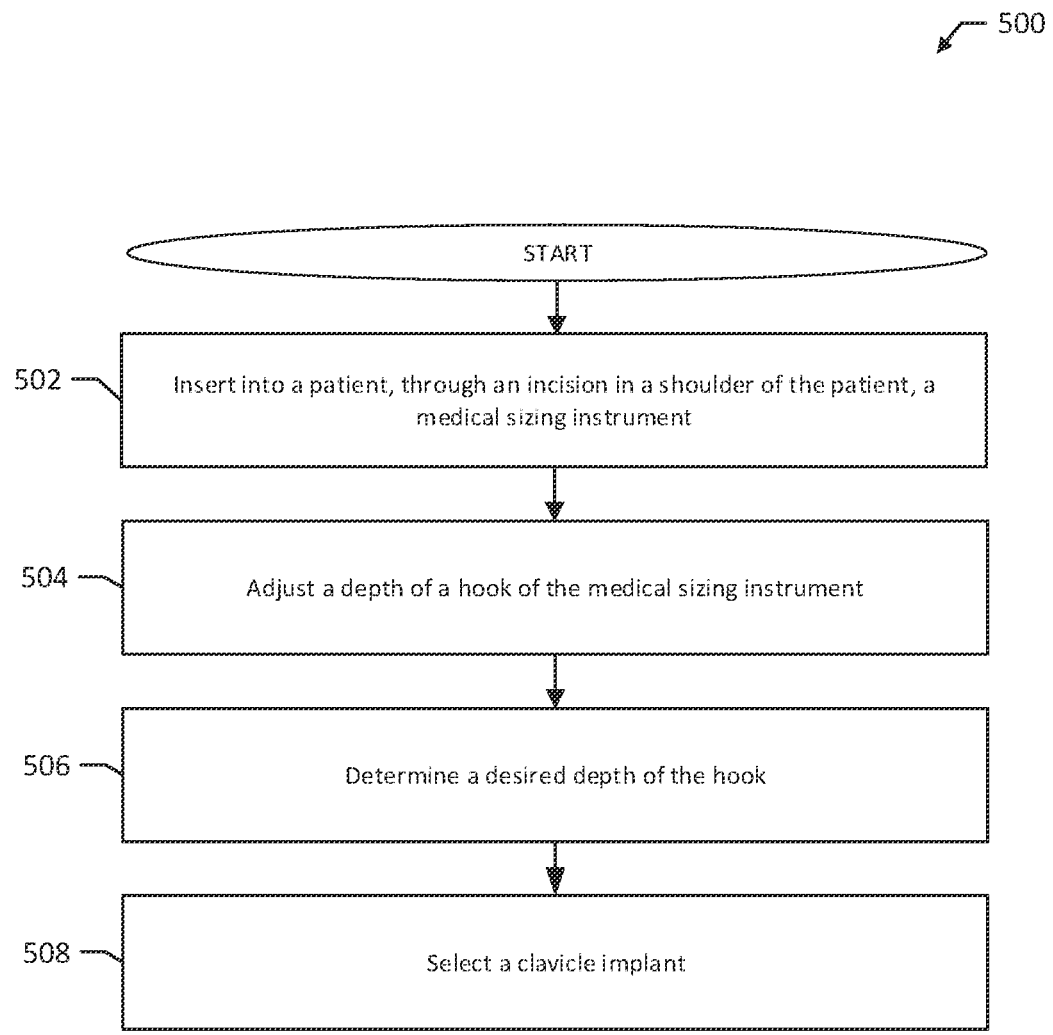
FIG. 5 illustrates a flow chart of an example method for determining an appropriate depth of a clavicle hook plate for a patient, according to an aspect of the present disclosure.

FIG. 5 illustrates a flowchart of an example method 500, according to an aspect of the present disclosure. Although the examples below are described with reference to the flowchart illustrated in FIG. 5, many other methods of performing the acts associated with FIG. 5 may be used. For example, the order of some of the blocks may be changed, certain blocks may be combined with other blocks, one or more of the blocks may be repeated, and some of the blocks described may be optional.

The example method 500 begins by inserting into a patient, through an incision in a shoulder of the patient, a medical sizing instrument (e.g., the medical sizing instrument 100) (block 502). The surgeon may insert the medical sizing instrument 100 such that the contoured plate 110 contacts the patient's clavicle. The surgeon may then adjust a depth of the hook (e.g., the hook 140) of the medical sizing instrument 100 (block 504). For example, a surgeon may rotate the handle 130 clockwise and/or counterclockwise to adjust the depth of the hook 140. The surgeon may then determine a desired depth of the hook 140 (block 506). For example, a surgeon may determine the depth of the hook 140 that the surgeon believes will best maintain the anatomical alignment of the patient's clavicle and acromion. The surgeon may then select a clavicle implant corresponding to the desired depth of the hook (block 508). In some instances, the surgeon may also determine a desired length of the clavicle implant using the medical sizing instrument. For example, the surgeon may use the contoured plate 110 and/or a member (e.g., the indexing ruler 466) that extends a measuring length of the contoured plate 110 to determine the desired implant length. The surgeon may then select a clavicle implant corresponding to the desired depth of the hook and the desired implant length.

Figure 6:
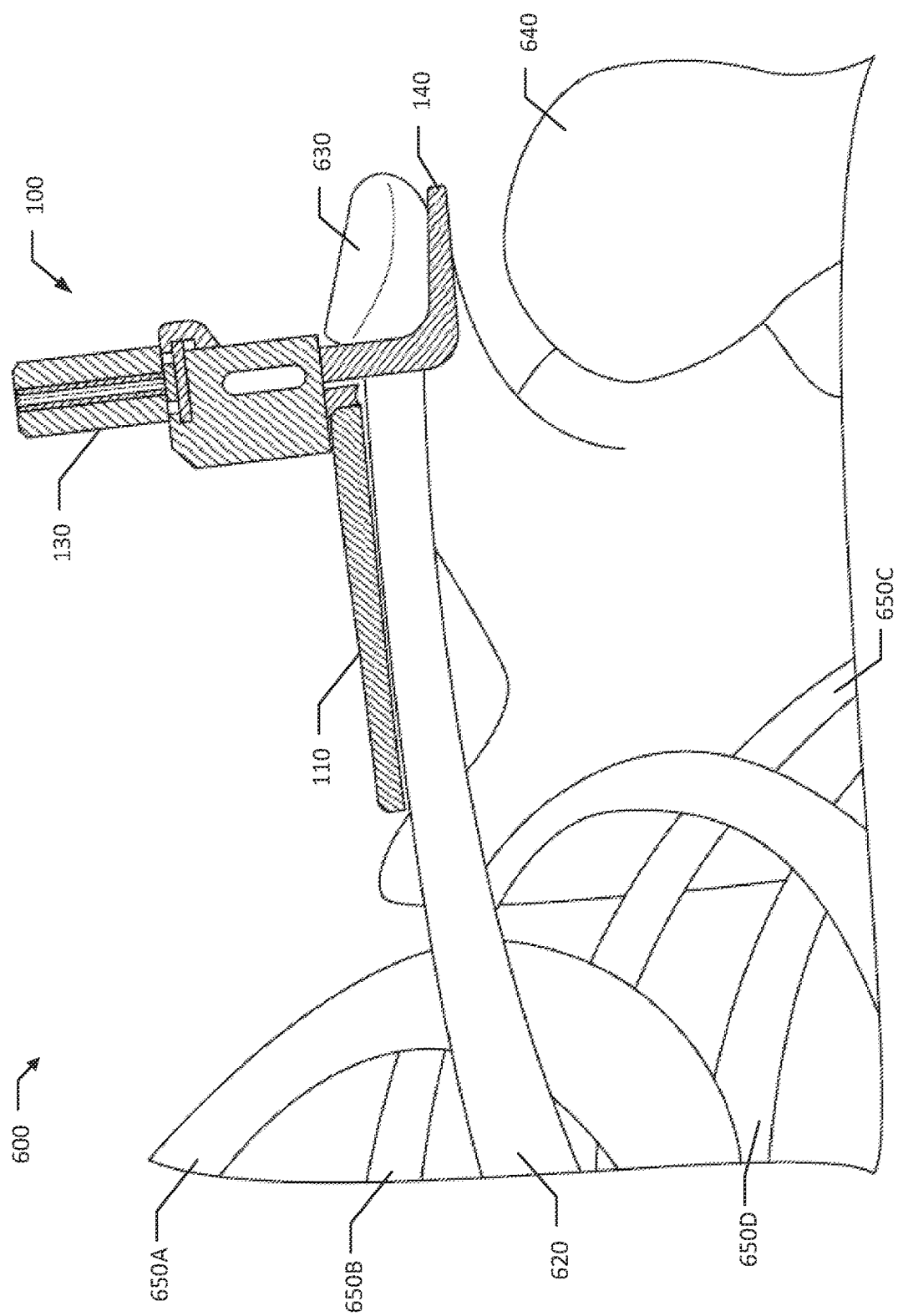
FIG. 6 illustrates an example medical sizing instrument inserted into a patient for determining an appropriate hook depth, according to an aspect of the present disclosure.

FIG. 6 illustrates an example medical sizing instrument 100 inserted into a patient 600 for determining an appropriate hook depth, according to an aspect of the present disclosure. The left side of the patient 600 is illustrated, and thus the medical sizing instrument 100 accordingly includes a plate contoured for the left side of a patient. For context, the humerus 640 and ribs 650A-D of the patient 600 are illustrated. Once a surgeon has made an incision in the shoulder of the patient 600 and obtained the appropriate exposure to the clavicle 620 and acromioclavicular joint of the patient 600, and performed any preliminary reduction steps needed, the surgeon inserts the medical sizing instrument 100. The surgeon inserts the medical sizing instrument 100 such that its plate (e.g., the contoured plate 110) is placed on the distal portion of the clavicle 620 and the hook (e.g., the hook 140) extends across the acromioclavicular joint under the acromion 630. This is the same position in which the clavicle hook plate is implanted once the appropriate sizing is determined.

In some instances, the surgeon may provisionally fix the medical sizing instrument 100 in place once positioned using instruments such as k-wires, plate tacks, and clamps. These, however, are not illustrated. Once the medical sizing instrument 100 is positioned, the surgeon may check the position and reduction of the distal portion of the clavicle 620 and/or the acromioclavicular joint based on the configuration of the medical sizing instrument 100. If the surgeon determines that the depth of the hook 140 is not correct, in some instances, the surgeon may adjust the depth of the hook 140 (e.g., rotate the handle 130) while the medical sizing instrument 100 remains in place, and may re-assess the position and reduction. In other instances, the surgeon may remove the medical sizing instrument 100 from the patient, adjust the depth of the hook 140, and then reinsert the medical sizing instrument 100 with the adjusted depth of the hook 140 prior to re-assessing the position and reduction.

Once the surgeon adjusts the depth of the hook 140 to a depth the surgeon determines provides a satisfactory reduction of the distal portion of the clavicle 620 and/or the acromioclavicular joint, the surgeon may read the determined depth off the medical sizing instrument 100. For instance, the surgeon may view an indicator (e.g., the indicator 258) on the hook 140 through a window (e.g., the window 218) in a tower (e.g., the tower 120) of the medical sizing instrument 100 in comparison to markings (e.g., the markings 220) on the tower 210 to read the determined depth, as described above. In some instances, the determined depth may be between two of the markings 220, and thus between two depth offerings in a clavicle hook plate system the surgeon is using. In such instances, the surgeon may use that information to determine which offered depth between the two is best for the patient, such as the offered depth that is closest to the determined depth. After the surgeon determines the appropriate hook depth for the patient, the surgeon may remove the medical sizing instrument 100 from the patient and select a clavicle hook plate with the determined appropriate hook depth for implantation.

Accordingly, the surgeon is able to determine the appropriate hook depth for the patient with just one template, the example medical sizing instrument 100. The surgeon may avoid having to swap out multiple templates to assess hook depth, which can be time-consuming and less accurate. For instance, when the ideal hook depth is between two offered hook depths, a surgeon can determine the ideal hook depth and use that information to decide which offered hook depth is best. A surgeon relying on multiple templates instead has to rely on the eye test and memory as the surgeon switches between the two templates on either end of the ideal hook depth.

Without further elaboration, it is believed that one skilled in the art can use the preceding description to utilize the claimed inventions to their fullest extent. The examples and embodiments disclosed herein are to be construed as merely illustrative and not a limitation of the scope of the present disclosure in any way. It will be apparent to those having skill in the art that changes may be made to the details of the above-described embodiments without departing from the underlying principles discussed. In other words, various modifications and improvements of the embodiments specifically disclosed in the description above are within the scope of the appended claims. For example, any suitable combination of features of the various embodiments described is contemplated.

The invention is claimed as follows:

1. A medical sizing instrument for clavicle hook plates comprising:
   a tower including an opening extending from a top end of the tower to a bottom end of the tower;
   a contoured plate extending from the tower, the contoured plate being shaped to match the contour and shape of a clavicle plate implant to be secured to a patient's clavicle bone; and
   a hook including a first portion at an angle to a second portion, wherein at least part of the second portion is positioned through the opening in the tower; and
   a handle,
   wherein the handle is configured to be engaged to adjust a distance between the first portion of the hook and the bottom end of the tower,
   wherein the first portion of the hook is disposed adjacent a bottom-most end of the tower, and
   wherein the contoured plate extends from the bottom-most end of the tower.

2. The medical sizing instrument of claim 1, wherein engaging the handle includes rotating the handle to adjust the distance between the first portion of the hook and the bottom end of the tower.

3. The medical sizing instrument of claim 1, wherein the second portion of the hook includes exterior threading, wherein the handle includes interior threading, and wherein the interior threading of the handle engages the exterior threading of the hook as the handle is engaged, thereby adjusting the distance between the first portion of the hook and the bottom end of the tower.

4. The medical sizing instrument of claim 3, wherein the handle is removably or fixedly secured to the tower.

5. The medical sizing instrument of claim 1, wherein the second portion of the hook includes the handle.

6. The medical sizing instrument of claim 5, wherein the second portion of the hook and the tower are configured such that engaging the handle includes translating the handle towards or away from the top end of the tower to adjust the distance between the first portion of the hook and the bottom end of the tower.

7. The medical sizing instrument of claim 1, wherein the contoured plate is integrally connected with the tower.

8. The medical sizing instrument of claim 1, wherein the first portion of hook extends from the second portion in a first direction relative to the tower, and wherein the contoured plate extends from the tower in a second direction, the first direction being substantially opposite the second direction.

9. The medical sizing instrument of claim 1, wherein the tower further includes a window and a plurality of markings adjacent the window, wherein the second portion of the hook includes an indicator marking, and wherein the indicator marking is visible through the window when the distance between the first portion of the hook and the bottom end of the tower is adjusted.

10. The medical sizing instrument of claim 1, wherein the second portion of the hook and the opening in the tower are configured such that the second portion of the hook may be positioned through the opening in the tower in only a single orientation.

11. The medical sizing instrument of claim 1, further comprising a member pivotally coupled to the contoured plate such that the member may be deployed to extend a measuring length of the contoured plate.

12. The medical sizing instrument of claim 1, wherein the medical sizing instrument is configured such that the hook may be temporarily locked into discrete positions when the handle is engaged to adjust the distance between the first end of the hook and the bottom end of the tower, each discrete position corresponding to a discrete distance between the first end of the hook and the bottom end of the tower.

* * * * *